(12) United States Patent
Woltman et al.

(10) Patent No.: US 8,231,591 B2
(45) Date of Patent: Jul. 31, 2012

(54) ABSORBENT ARTICLE WITH LENGTHWISE, COMPACT-FOLD

(75) Inventors: Garry Roland Woltman, Appleton, WI (US); Carrie Nicole Pateras, Appleton, WI (US); Angela Rae Heck, Appleton, WI (US); Karyn Clare Schroeder, Neenah, WI (US); Marcille Faye Ruman, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1497 days.

(21) Appl. No.: 11/408,324

(22) Filed: Apr. 21, 2006

(65) Prior Publication Data

US 2007/0250028 A1 Oct. 25, 2007

(51) Int. Cl.
*A61F 13/15* (2006.01)
*A61F 13/20* (2006.01)
(52) U.S. Cl. ........ 604/385.01; 604/385.02; 604/385.201
(58) Field of Classification Search ............. 604/385.02, 604/385.04, 385.01
See application file for complete search history.

(56) References Cited

U.S. PATENT DOCUMENTS

| | | | |
|---|---|---|---|
| 2,693,439 A | 11/1954 | Page et al. | |
| 2,772,678 A | 12/1956 | Walter | |
| 3,667,458 A | 6/1972 | Krebs | |
| 4,023,570 A | 5/1977 | Chinai et al. | |
| 4,061,820 A | 12/1977 | Magid et al. | |
| 4,195,634 A | 4/1980 | DiSalvo et al. | |
| 4,336,804 A | 6/1982 | Roeder | |
| 4,337,772 A | 7/1982 | Roeder | |
| 4,376,440 A | 3/1983 | Whitehead et al. | |
| 4,475,913 A | 10/1984 | Hlaban | |
| 4,556,146 A | 12/1985 | Swanson et al. | |

(Continued)

FOREIGN PATENT DOCUMENTS

BE 884898 A 2/1981

(Continued)

OTHER PUBLICATIONS

Zander, Teresa and Tom Keenan, "Improved Feminine Care Articles," published at IP.com as Document 132508D, Dec. 19, 2005, available online at "http://www.priorartdatabase.com/IPCOM/000132508D", 4 pages.

*Primary Examiner* — Michele M Kidwell
(74) *Attorney, Agent, or Firm* — Randall W. Fieldhack; David J. Arteman

(57) ABSTRACT

A personal care article (20) has a longitudinal-direction (22), a lateral cross-direction (24), a first end-section (72), a second end-section (72a), and an intermediate-section (76) interposed between the first end-section (72) and the second end-section (72a). At least a portion of the first end-section has been folded along or otherwise includes a first end-fold-region (64) which is substantially convex along a backsheet-side of the article. At least a portion of the second end-section has been folded along or otherwise includes a second end-fold-region (66) which is substantially convex along the backsheet-side of the article. In other aspects, the article can include a first, lengthwise-fold-region (58) in the first end-section, a second, lengthwise-fold-region (62) in the second end-section, and a third, lengthwise-fold-region (68) in the intermediate section. Additionally, the first lengthwise-fold-region can have a first, fold-direction that is opposite a third, fold-direction of the third lengthwise-fold-region.

15 Claims, 12 Drawing Sheets

U.S. PATENT DOCUMENTS

| | | |
|---|---|---|
| 4,631,062 A | 12/1986 | Lassen et al. |
| 4,753,645 A | 6/1988 | Johnson |
| 4,802,884 A | 2/1989 | Froidh et al. |
| 4,950,264 A | 8/1990 | Osborn |
| 4,959,265 A | 9/1990 | Wood et al. |
| 5,011,480 A | 4/1991 | Gossens et al. |
| 5,088,993 A | 2/1992 | Gaur |
| 5,197,959 A | 3/1993 | Buell |
| 5,221,276 A | 6/1993 | Battrell |
| 5,387,450 A | 2/1995 | Stewart |
| 5,453,296 A | 9/1995 | Lauritzen et al. |
| 5,484,636 A | 1/1996 | Berg, Jr. et al. |
| 5,591,153 A | 1/1997 | Mattingly |
| 5,611,790 A | 3/1997 | Osborn et al. |
| 5,662,758 A | 9/1997 | Hamilton et al. |
| H1698 H | 11/1997 | Lloyd et al. |
| 5,694,739 A | 12/1997 | Mattingly |
| 5,769,837 A | 6/1998 | Parr |
| 5,993,430 A | 11/1999 | Gossens et al. |
| 6,004,308 A | 12/1999 | Haddock |
| 6,168,582 B1 | 1/2001 | Hasegawa |
| 6,176,850 B1 | 1/2001 | Rosenfeld et al. |
| 6,186,993 B1 | 2/2001 | Toyoshima et al. |
| 6,293,932 B1 | 9/2001 | Balzar et al. |
| 6,394,990 B1 | 5/2002 | Rosenfeld et al. |
| 6,436,080 B1 | 8/2002 | Carlucci et al. |
| 6,565,549 B1 | 5/2003 | Allen et al. |
| 6,572,600 B1 | 6/2003 | Roe et al. |
| 6,575,947 B1 | 6/2003 | Tameishi et al. |
| 6,695,827 B2 | 2/2004 | Chen et al. |
| 6,805,691 B2 * | 10/2004 | Kashiwagi et al. ...... 604/385.02 |
| 7,427,277 B2 | 9/2008 | Woltman et al. |
| 7,708,727 B2 | 5/2010 | Woltman et al. |
| 2003/0014032 A1 | 1/2003 | Kashiwagi et al. |
| 2004/0018365 A1 | 1/2004 | Krautkramer et al. |
| 2004/0163179 A1 | 8/2004 | Trefethren et al. |
| 2004/0167489 A1 | 8/2004 | Kellenberger et al. |
| 2004/0186448 A1 | 9/2004 | Misek et al. |
| 2005/0085780 A1 | 4/2005 | Corlett |
| 2005/0085781 A1 | 4/2005 | Corlett |
| 2005/0131371 A1 | 6/2005 | Fell et al. |
| 2005/0182374 A1 | 8/2005 | Zander et al. |
| 2005/0251101 A1 | 11/2005 | Becker |
| 2007/0078425 A1 | 4/2007 | Pateras et al. |
| 2007/0250031 A1 | 10/2007 | Woltman et al. |

FOREIGN PATENT DOCUMENTS

| | | |
|---|---|---|
| EP | 0 313 426 A1 | 4/1989 |
| EP | 0 688 549 A2 | 12/1995 |
| EP | 0 471 384 B1 | 10/1996 |
| EP | 0 850 628 A1 | 7/1998 |
| EP | 1 407 747 A1 | 4/2004 |
| FR | 2 765 474 A1 | 1/1999 |
| GB | 2 267 830 A | 12/1993 |
| GB | 2 298 627 A | 9/1996 |
| GB | 2 380 138 A | 4/2003 |
| JP | 11-056901 A | 3/1999 |
| JP | 2006-103689 A | 4/2006 |
| WO | WO 92/00400 A1 | 3/1992 |
| WO | WO 96/20668 A1 | 7/1996 |
| WO | WO 99/55270 A1 | 11/1999 |
| WO | WO 00/21477 A1 | 4/2000 |
| WO | WO 2005/060894 A1 | 7/2005 |

* cited by examiner

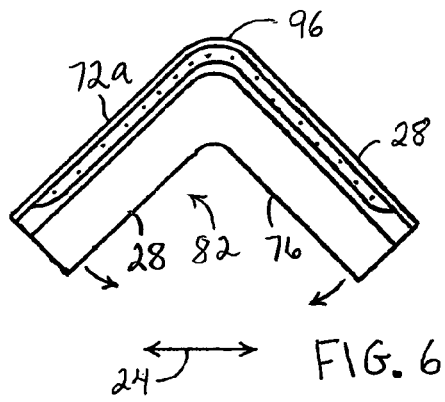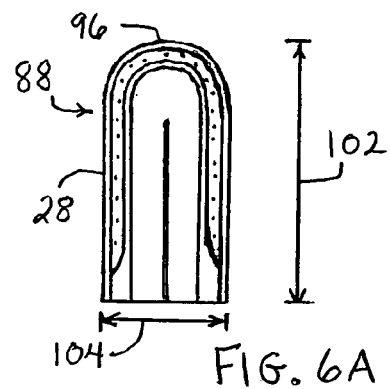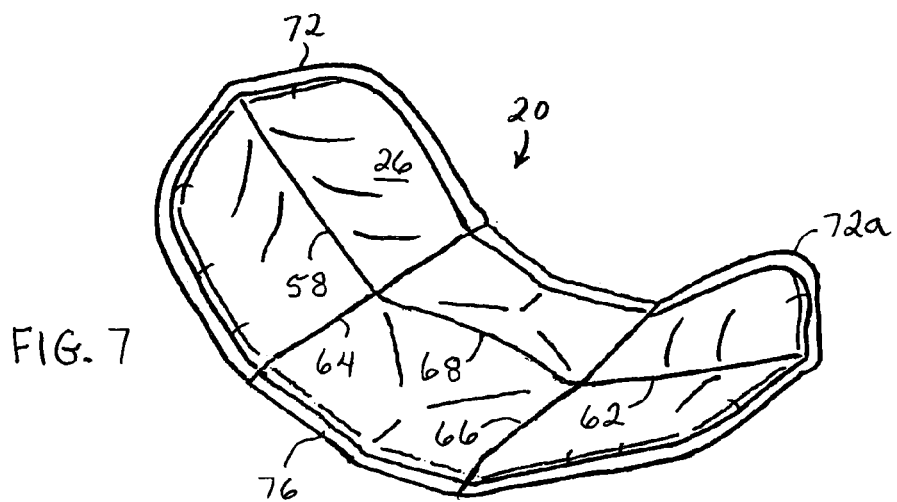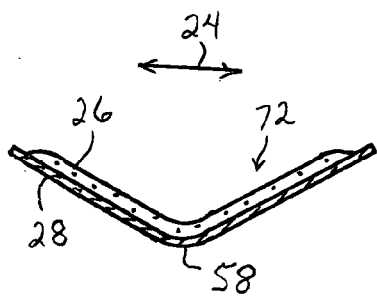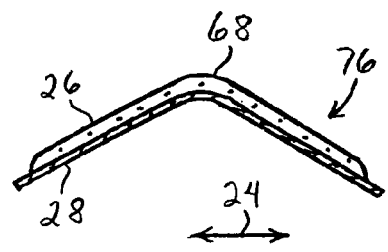

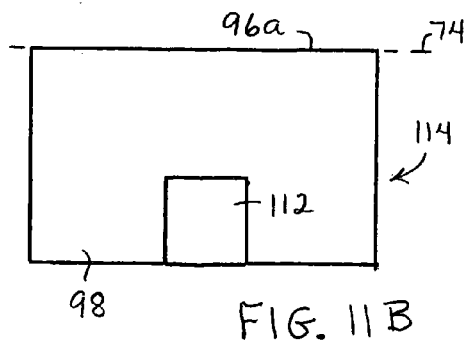
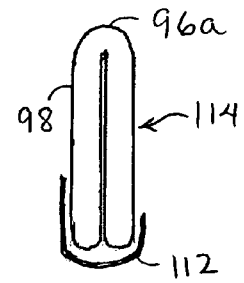
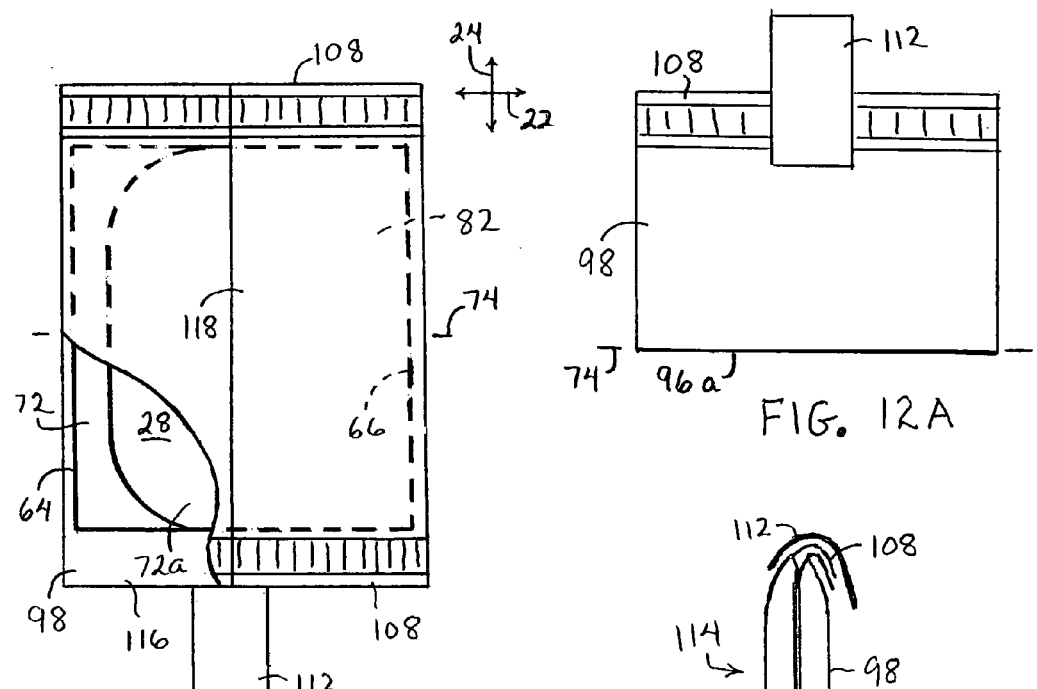
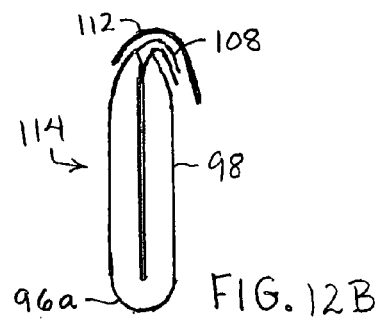

ABSORBENT ARTICLE WITH LENGTHWISE, COMPACT-FOLD

FIELD OF THE INVENTION

The present invention relates to a personal care article. More particularly, the present invention pertains to a personal care absorbent article, such as an absorbent feminine care or adult care pad. The personal care article can be operatively secured to a selected garment of a wearer.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that feminine care articles have been employed to absorb and hold liquids, such as urine and/or menses. The absorbent articles have included various systems of liquid-handling layers, such as intake layers, distribution layers, retention layers and the like. The absorbent products are worn against the body. To keep these products on the body, the products have included either a system of fasteners or a garment attachment system. For example, feminine care articles have employed a garment-attachment adhesive to help secure the article to a wearer's undergarment. Additionally, the absorbent articles have included wing portions which can help to hold the article in place at a selected location in the undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners. Individual absorbent articles have been folded or rolled to reduce the size of the article for storage and transport prior to use, and each article has been enclosed in a corresponding, individual storage pouch or other container.

The absorbent products undergo deformation during wear, and the deformation has caused the product to take undesired shapes or configurations. The product can fold and shift to increase the likelihood of fluid leakage onto the wearer or the wearer's clothing, or to increase the exposure of the wearer or the wearer's clothing to undesired regions of the product. In particular situations, the deformation has caused the fasteners or garment attachment system to detach and come in contact with the wearer. The contact has caused excessive irritation and discomfort, particularly when a garment-attachment adhesive has contacted the wearer's skin or hair. The occurrences of the undesirable deformations and configurations increase when the absorbent article has been constructed with greater flexibility and thinness.

Conventional absorbent articles have been folded or rolled for placement in a storage pouch. Particular storage configurations, however, can increase the occurrences of the undesired deformations of the absorbent article. Additionally, the storage configurations have not provided desired combinations of small size, discretion, ease of use. As a result, there has been a continued need for improved absorbent articles that can be discreetly carried in a person's hand, provide desired levels of liquid intake and retention, provide a desired ease of securement to a wearer's undergarment, and provide desired levels of comfort to the wearer.

BRIEF DESCRIPTION OF THE INVENTION

Generally stated, the present invention provides an article having a longitudinal direction, a relatively shorter lateral cross-direction, first and second longitudinally opposed end-sections, and an intermediate section located between the end portions. The article includes a liquid permeable topsheet layer, and a backsheet layer which is operatively connected to the topsheet layer. At least an operative portion of said first end-section has been folded along a first laterally-extending, end-fold-region which is substantially convex along a backsheet-side of the article and extends along at least a major portion of a corresponding lateral width of the first end-fold-region. At least an operative portion of the second end-section has been folded along a second laterally-extending, end-fold-region which is substantially convex along the backsheet-side of the article and extends along at least a major portion of a corresponding lateral width of the second end-fold-region. In particular aspects, at least an operative portion of the first end-section has been folded along a first, lengthwise-fold-region, which is positioned to extend longitudinally along a major portion of the first end-section, and at least an operative portion of said second end-section has been folded along a second, lengthwise-fold-region, which is positioned to extend longitudinally along a major portion of the second end-section. In another aspect, at least an operative portion of the intermediate-section has been folded along a third lengthwise-fold-region, which is positioned to extend longitudinally along a major portion of the intermediate-section. In further aspects, the first lengthwise-fold-region has been folded in a first, fold-direction, the second lengthwise-fold-region has been folded in a second, fold-direction, the third lengthwise-fold-region has been folded in a third, fold-direction; where the first fold-direction is substantially the same as the second fold-direction, and the third fold-direction is substantially opposite the first fold-direction. Accordingly, the third fold-direction can be substantially opposite the second fold-direction.

By incorporating its various features and configurations, the article can better provide desired combinations of small size, discretion, protection, comfort and ease of use. The articles can, for example, be more discreetly carried in a person's hand, and can provide enhanced protection against the leakage of liquids. The article can include fold regions to create areas of controlled deformation. When the wearer's thighs come in contact with the lateral sides of the center or intermediate portion of the pad, the article can deform along the fold lines or fold regions. In a particular aspect, the deformation can allow one or more desired sections of the article to move away from the body. In another aspect, the deformation can allow one or more sections of the article to move closer to the body. As a result, the article can have configurations that better absorb urine or menstrual fluid. Where the article includes a garment-attachment mechanism (e.g. adhesive), for example, the configurations of the article can help avoid excessive skin irritation caused by the garment-attachment mechanism, and can help avoid undesired attachments of the garment-attachment mechanism to other portions of the article or to the body of a wearer.

BRIEF DESCRIPTION OF THE DRAWINGS

The various features, aspects and advantages of the present invention will become better understood with reference to the following description, appended claims and accompanying drawings where:

FIG. 6 shows a representative, schematic, end view of an article that has been partially subjected to a first arrangement of a composite folding operation to provide a composite-fold-region.

FIG. 6A shows a representative, schematic, end view of an article that has been completely subjected to the first, composite folding operation.

FIG. 7 shows a representative, perspective view of a partially unfolded article that has been subjected to the first arrangement of the composite folding operation.

FIG. 7A shows a representative, cross-sectional view of an end section of an article that includes a corresponding, lengthwise fold-region produced by the first, composite folding operation.

FIG. 7B shows a representative, cross-sectional view of an intermediate section of an article that includes a corresponding, lengthwise, intermediate fold-region produced by the first, composite folding operation.

FIG. 11B representatively shows the wrapped article of FIG. 10A folded about a composite fold-line to provide a composite-folded, wrapped article, and secured with a wrap retainer mechanism.

FIG. 11C shows a schematic, partially-expanded, end view of the composite-folded, wrapped article illustrated in FIG. 10B.

FIG. 12 shows another representative arrangement of an article contained in a pouch or other wrap member.

FIG. 12A representatively shows the wrapped article of FIG. 11 folded about a composite fold-line to provide another composite-folded, wrapped article.

FIG. 12B shows a schematic, partially-expanded, end view of the composite-folded, wrapped article illustrated in FIG. 11A, in which side margins of the wrap member have been inwardly folded onto a container portion of the wrap member, and the composite-folded, wrapped article has been secured with a wrap retainer mechanism.

DETAILED DESCRIPTION OF THE INVENTION

Figure 1:
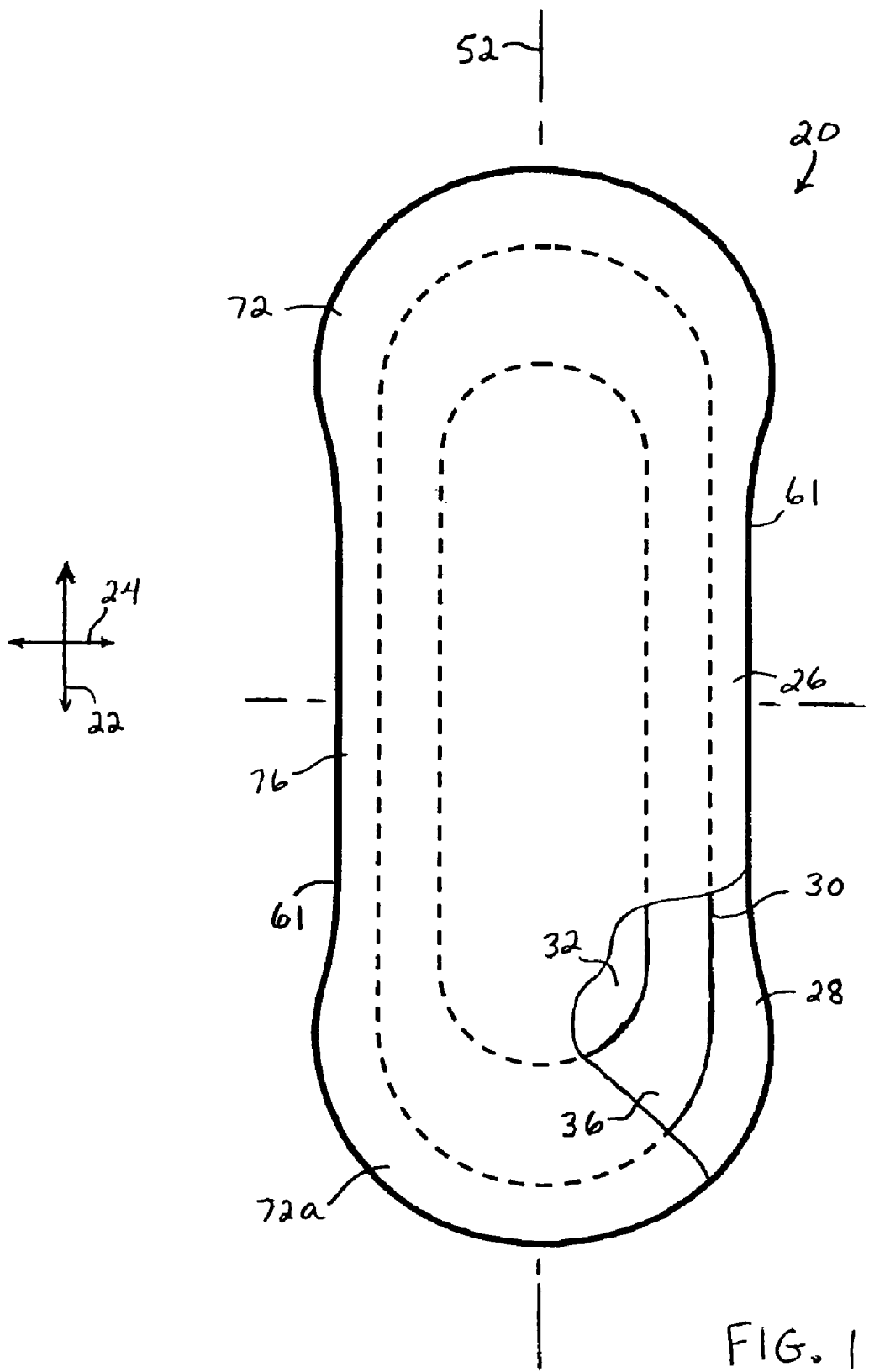
FIG. 1 shows a representative, partially cut-away, top, plan view of a bodyside of a representative article.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic. When comparing materials, a material that forms a relatively larger contact angle with water is relatively less hydrophilic than a material that forms a smaller contact angle with water.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, an operatively liquid-impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 2:
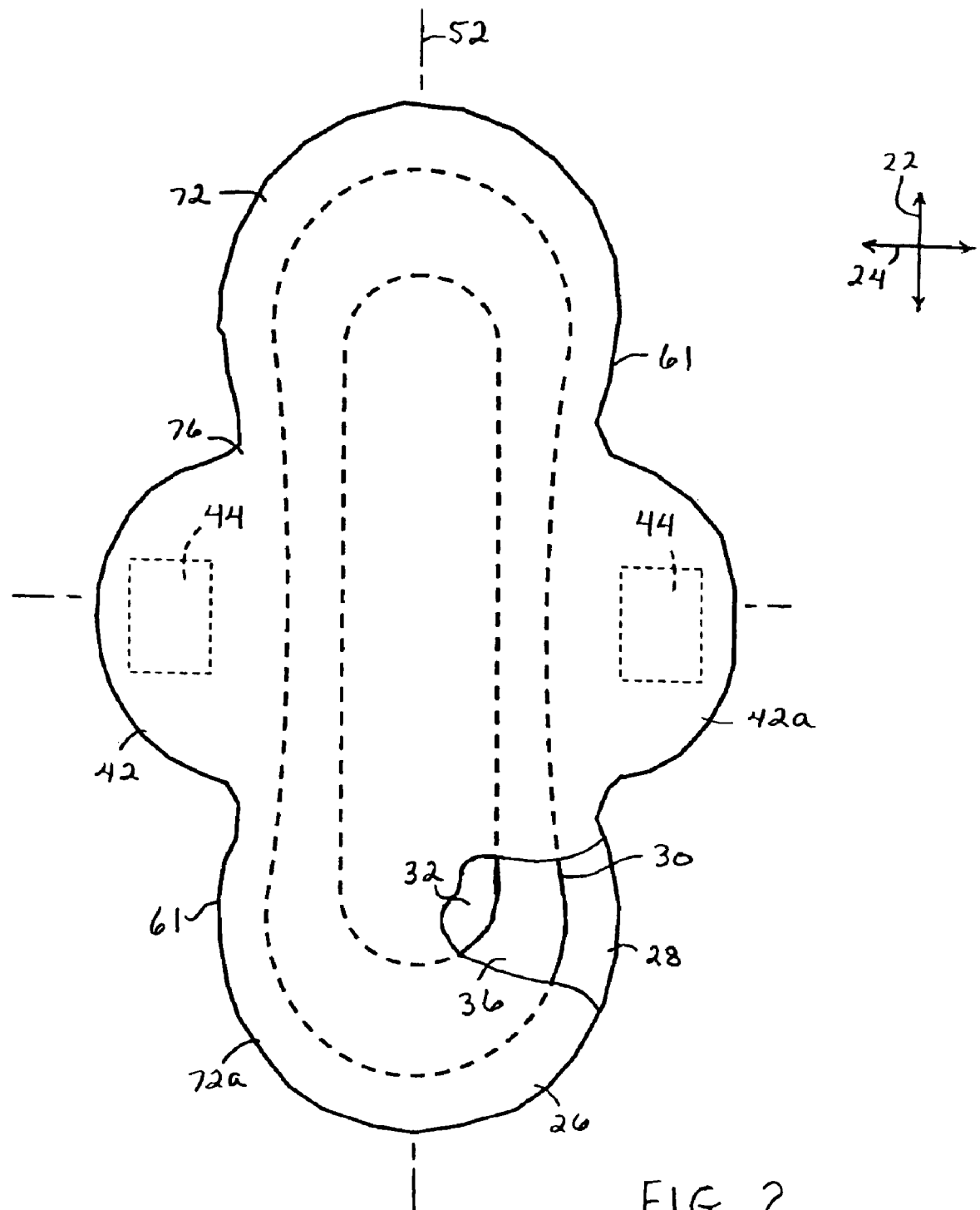
FIG. 2 shows a representative, partially cut-away, top, plan view of a bodyside of an article having side-panels or wings.
Figure 2A:
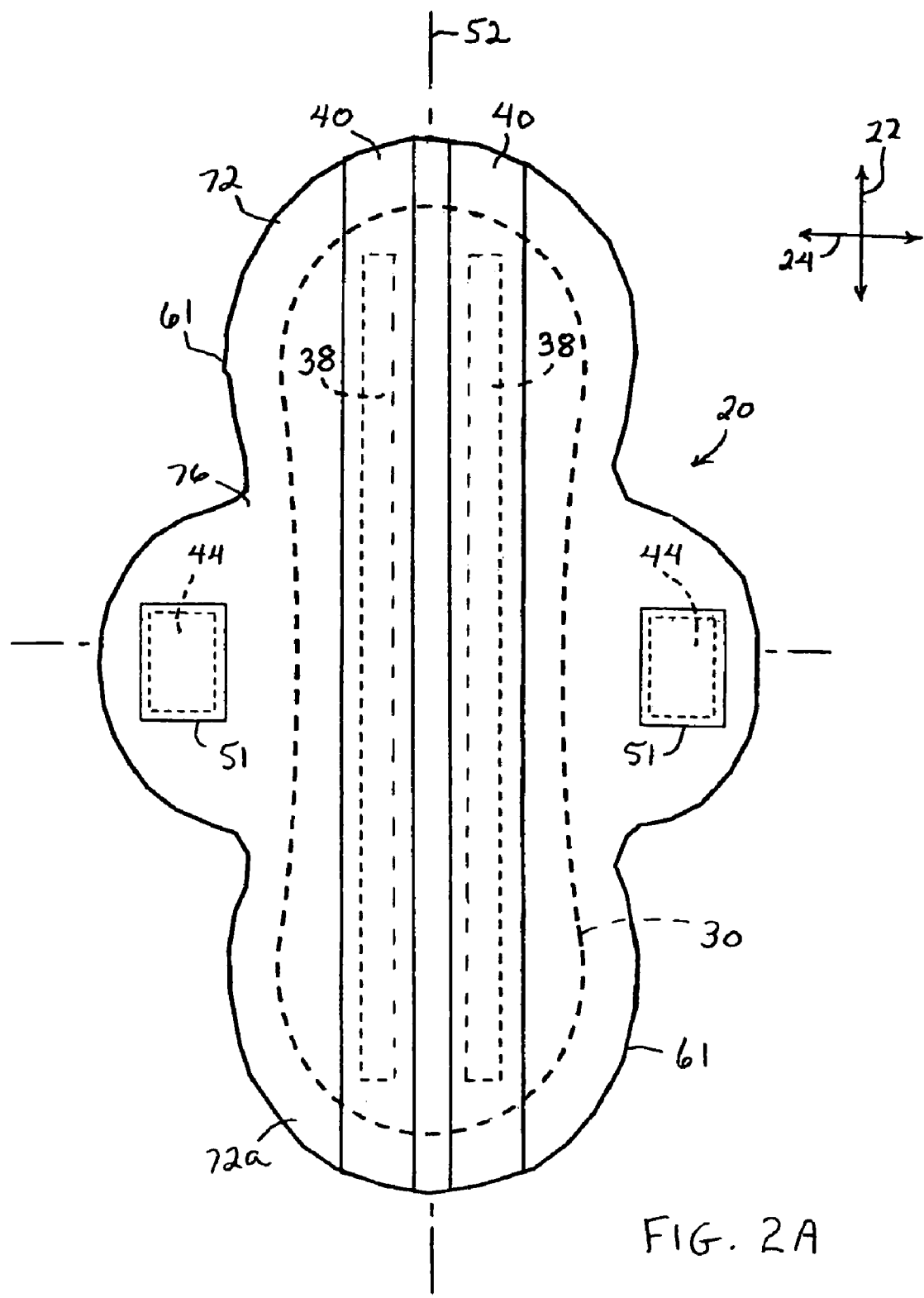
FIG. 2A shows a representative, bottom, plan view of a garment-side of the article illustrated in FIG. 2.
Figure 2B:
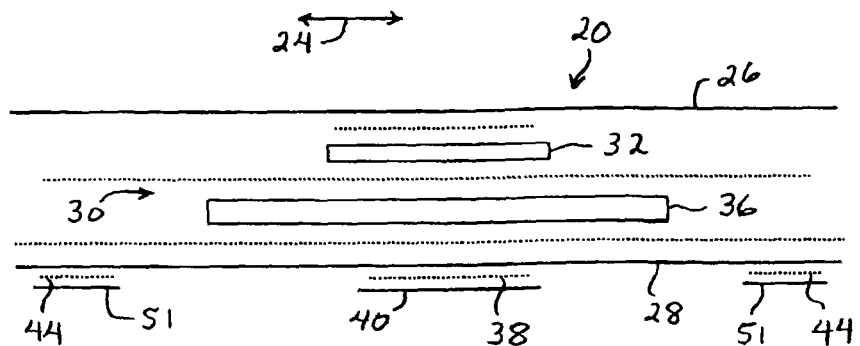
FIG. 2B shows an expanded, schematic view of a representative, transverse cross-section of the article illustrated in FIG. 2.
Figure 2C:
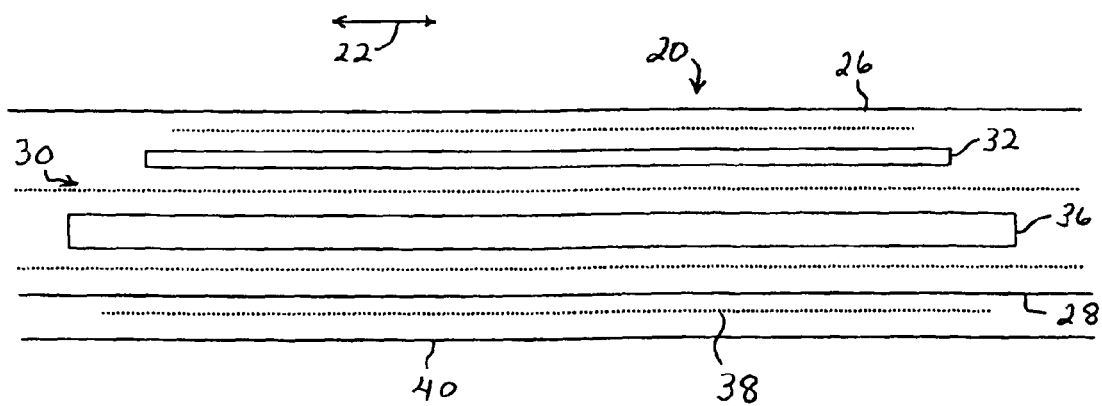
FIG. 2C shows an expanded, schematic view of a representative, longitudinal cross-section of the article illustrated in FIG. 2.

Personal care articles are well known in the art, and any personal care article may be reconfigured to incorporate the present invention. FIGS. 1 through 2C, illustrate examples of a suitable personal care article 20, such as the representatively shown adult care article, which is configured to incorporate the present invention. The adult care article can, for example, be an adult incontinence product, a feminine care liner, a feminine care pad or napkin, or the like.

Figure 3:
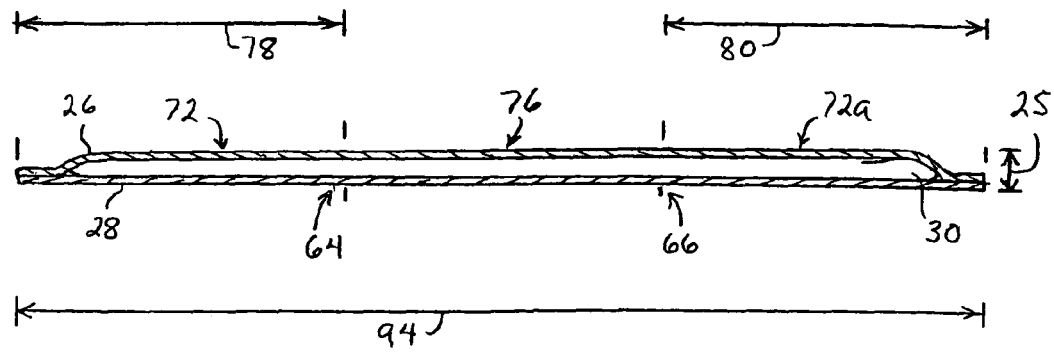
FIG. 3 shows a schematic view of a representative, longitudinal cross-section of a personal care article where the article has been arranged to be substantially flat and unfolded.
Figure 3A:
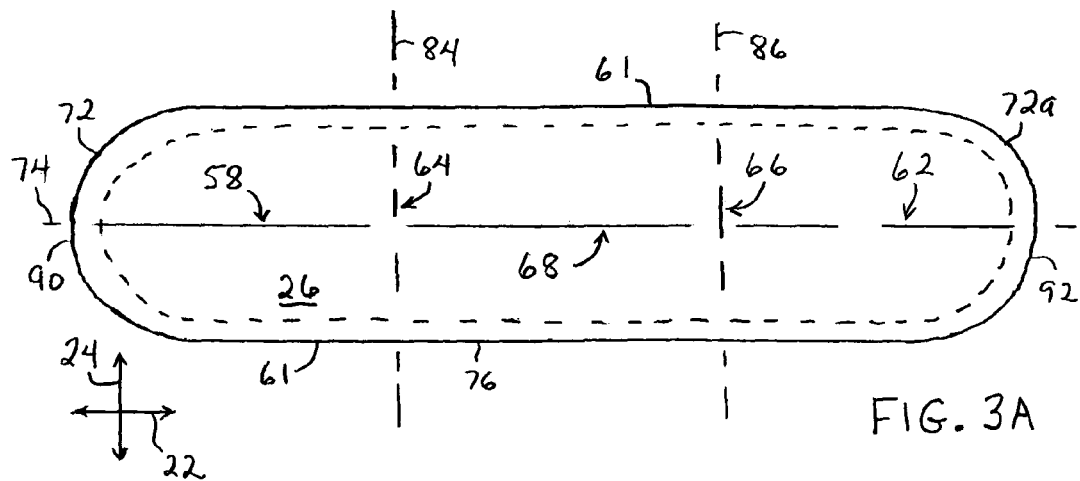
FIG. 3A shows a representative, plan view of a bodyside of a personal care article where the article has been arranged to be substantially flat and unfolded.
Figure 4:
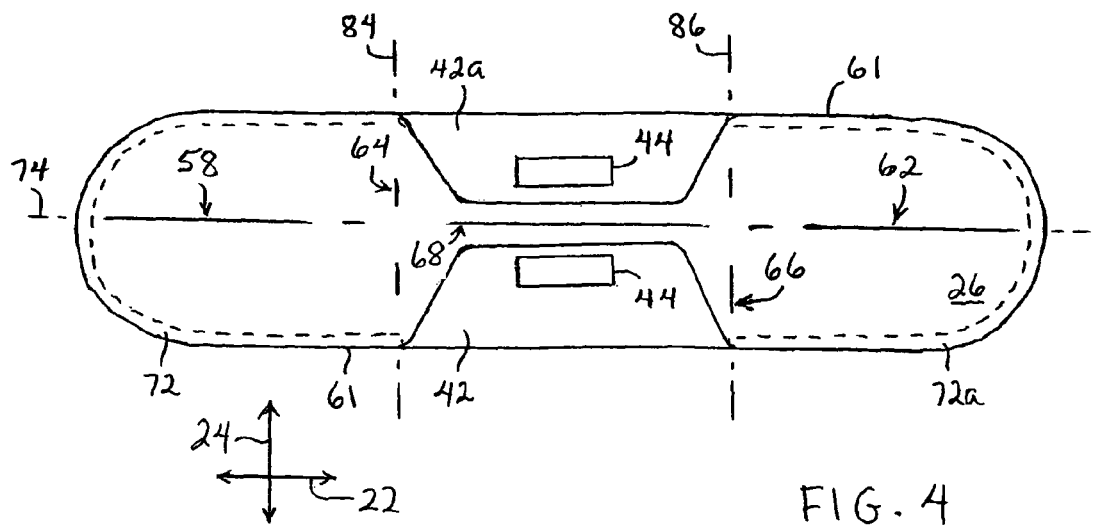
FIG. 4 shows a plan view of a bodyside of a representative article having side-panels or wings arranged in a storage position.

The individual article 20 can have a longitudinal-direction 22, a relatively shorter, lateral cross-direction 24, and a thickness-direction 25 (e.g. FIG. 3). The cross-direction extends generally perpendicular to the longitudinal-direction, and the thickness or z-direction extends generally perpendicular to both the longitudinal-direction and cross-direction. The article also has a first end-section 72, a second end-section 72a, and an intermediate-section 76. Desirably, the intermediate section is contiguous with and interposed between the first end-section 72 and the second end-section 72a. The article includes a liquid permeable topsheet layer 26, and a backsheet layer 28 which is operatively connected to the topsheet layer 26. Optionally, the article may include an absorbent body 30 which is operatively sandwiched between the topsheet and backsheet layers.

With reference to FIGS. 3 through 5B, at least an operative portion of the first end-section 72 has been transversely folded along a first laterally-extending, end-fold-region 64 which is substantially convex along a backsheet-side of the article and extends along at least a major portion of a corresponding lateral width of the first end-fold-region. The first end-fold-region can also be substantially concave along a topsheet-side of the article 20. In addition, at least an operative portion of the second end-section 72a has been transversely folded along a second laterally-extending, end-fold-region 66 which is substantially convex along the backsheet-side of the article and extends along at least a major portion of a corresponding lateral width of the second end-fold-region. The second end-fold-region can also be substantially concave along the topsheet-side of the article 20.

In particular aspects of the article, at least an operative portion of the first end-section 72 has been folded along a first, lengthwise-fold-region 58, which is positioned to extend longitudinally along a major portion of the first end-section Additionally, at least an operative portion of said second end-section 72*a* has been folded along a second, lengthwise-fold-region 62, which is positioned to extend longitudinally along a major portion of the second end-section. In another aspect, at least an operative portion of the intermediate-section 76 has been folded along a third lengthwise-fold-region 68, which is positioned to extend longitudinally along a major portion of the intermediate-section. In further aspects, the first lengthwise-fold-region 58 has been folded in a first, fold-direction, the second lengthwise-fold-region 62 has been folded in a second, fold-direction, and the intermediate, third lengthwise-fold-region 68 has been folded in a third, fold-direction. The first fold-direction is substantially the same as the second fold-direction, and the third fold-direction is substantially opposite the first fold-direction. Additionally, the third fold-direction can also be substantially opposite the second fold-direction.

In representatively shown aspects, the first, extending, lengthwise-fold-region 58, can be positioned to extend between the first end-fold-region 64 and a first terminal end-edge 90 of the article 20, and the second, longitudinally-extending, lengthwise-fold-region 62 can be positioned to extend between the second end-fold-region 66 and a second terminal end-edge 92 of the article 20. The third, longitudinally-extending, lengthwise, intermediate-fold-region 68 can be positioned to extend between the first end-fold-region 64 and the second end-fold-region 66. The article 20 can also include a garment-attachment mechanism for operatively securing the article to a wearer's undergarment. In desired aspects, each of the first, second and/or third lengthwise-fold-regions can extend substantially continuously along the entirety of its individual length. Each lengthwise-fold-region may optionally extend discontinuously along its individual length. Further aspects and features are set forth in the present disclosure.

By incorporating its various features and configurations, the article can better provide desired combinations of small size, discretion, protection, comfort and ease of use. The articles can be more discreetly carried in a person's hand, and can provide desired levels of fit, liquid intake and liquid retention. Where, for example, the intermediate section 76 of the article includes the selected lengthwise fold-region, the article can provide a selected fit against the wearer's body, and can provide a selected arrangement for receiving liquids discharged from the wearer. Where the article includes a garment-attachment mechanism (e.g. adhesive), the article configurations can help avoid the occurrence of excessive skin irritation from the garment-attachment mechanism, and can help avoid the occurrence of undesired attachments of the garment-attachment mechanism to other portions of the article or to the wearer's body.

In the various configurations of the article 20, the topsheet 26 may include a layer constructed of any operative material, and may be a composite material. For example, the topsheet layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded web, a bicomponent spunbond fabric or the like, as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. A more particular example of a suitable topsheet layer material can include a bonded-carded web composed of polypropylene and polyethylene, such as has been used as a topsheet stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material.

In desired arrangements, the topsheet layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. Typically intended to contact the wearer's skin, the topsheet layer 26 can be configured to provide comfort and conformability, and can function to direct bodily exudates away from the body and toward the absorbent structure 30. In a desired feature, the topsheet layer 26 can be configured to retain little or no liquid in its structure, and can be configured to provide a relatively comfortable and non-irritating surface next to the body tissues of a female wearer. The topsheet layer 26 can be constructed of any material which is also easily penetrated by bodily fluids that contact the bodyside surface of the topsheet layer. Additionally, the topsheet layer may optionally be configured to provide a small or other selected, operative amount of absorbent, liquid-retention capacity.

The topsheet 26 can also have at least a portion of its bodyside surface treated with a surfactant to render the topsheet more hydrophilic. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

Where the article includes the absorbent body 30, the topsheet 26 may be maintained in secured relation with the absorbent structure by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the absorbent.

The topsheet 26 typically extends over the upper, bodyside surface of the absorbent structure, but can optionally extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins of the topsheet and backsheet can be joined together to partially or entirely, surround or enclose the absorbent structure.

The backsheet 28 can be operatively connected to the topsheet layer 26 using any suitable technique or any direct or indirect configuration. The connection technique may, for example, include adhesive bonding, thermal bonding, sonic bonding, cohesive bonding, mechanical attachments or the like, as well as combinations thereof. The backsheet layer may include a layer constructed of any operative material, and may or may not have a selected level of liquid-permeability or an operative level of liquid-impermeability, as desired. In a particular configuration, the baffle or backsheet 28 may be configured to provide an operatively liquid-impermeable backsheet structure. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the backsheet 28 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable backsheet available from Hanjin Printing, Hanjin P&C Company Limited, a business having offices located in Sahvon-li.Jungan-mvu.Kongiu-City, Chung cheong nam-do, Republic of South Korea. The backsheet material is a breathable film, which is white in color, dimple embossed, and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., U.S.A.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural fiber (e.g. woodpulp fluff) and/or synthetic fiber. Additionally, the absorbent body may include one or more components that can modify menses or intermenstrual liquids.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the absorbent article.

The amount of superabsorbent material in the absorbent body 30 can be up to about 75 wt % or more, as determined with respect to the total weight of material in the absorbent body. In particular aspects, the amount of superabsorbent material can be within the range of about 5-35 wt %, and can alternatively be within the range of about 8-20 wt % to provide desired performance. In desired configurations, the amount of superabsorbent can be about 15 wt %.

In particular configurations, the absorbent body 30 can be included in an absorbent article, and can provide a composite, overall absorbent saturation capacity (saturated retention capacity) which is at least a minimum of about 20 grams of 0.9 wt % saline, as determined under substantially unconstrained, free-swell conditions. The overall absorbent capacity can alternatively be at least about 100 grams of 0.9 wt % saline to provide improved performance. In other aspects, the overall absorbent saturation capacity can be up to a maximum of about 500 grams of 0.9 wt % saline or more, and can alternatively be up to about 300 grams of 0.9 wt % saline to provide improved effectiveness. In a desired arrangement, the composite, overall absorbent capacity can be about 150 grams of 0.9 wt % saline.

In other configurations, the absorbent body 30 can be included in a feminine care article, and can provide a composite, overall absorbent saturation capacity which is at least a minimum of about 5.5 grams of menses simulant A. The overall absorbent saturation capacity can alternatively be at least about 40 grams of menses simulant A to provide improved performance. In other aspects, the overall absorbent saturation capacity can be up to a maximum of about 120 grams of menses simulant A, or more, and can alternatively be up to about 88 grams of menses simulant A to provide improved effectiveness. In a desired arrangement, the composite, overall absorbent saturation capacity can be about 60 grams of menses simulant A.

In particular configurations, the absorbent body 30 can be included in a feminine care article, and can provide a composite, overall absorbent retention capacity which is at least a minimum of about 5 grams of menses simulant A. The overall absorbent retention capacity can alternatively be at least about 10 grams of menses simulant A to provide improved performance. In other aspects, the overall absorbent retention capacity can be up to a maximum of about 34 grams of menses simulant A, or more, and can alternatively be up to about 20 grams of menses simulant A to provide improved effectiveness. In a desired arrangement, the composite, overall absorbent retention capacity can be about 14.5 grams of menses simulant A.

The menses simulant A is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed. Simulant A is typically used for absorbent capacity tests, where the viscoelastic properties that affect liquid movement have been found to be of little importance.

The absorbent body 30 can include any operative configuration, and may, for example, include a single unitary layer, or multiple layers, as desired. As representatively shown, the absorbent body 30 of the selected article can comprise a composite structure having a selected plurality of strata or layers. With reference to FIGS. 2B and 2C, for example, the absorbent composite can include an intake layer 32 and an absorbent shaping layer 36, as well as any other desired components, arranged in any operative combination. As representatively shown, the structure of the absorbent body can include an absorbent pad, shaping layer 36 which is positioned between the topsheet 26 and the backsheet 28, and can include an intake layer 32 which is positioned between the topsheet 26 and the shaping layer 36.

In a particular aspect, the article 20 can include a top, bodyside intake layer 32 which is sized and placed to more effectively operate in a target area of the absorbent body 30 where liquids are more likely to be introduced into the article. The material of the intake layer can be configured to provide desired liquid-intake properties, substantially without consideration for delivering shaping properties. For example, the configuration of the intake layer may or may not include properties that are configured to prevent bunching and twisting of the article, particularly the absorbent structure, during ordinary wear.

The intake layer can include material that is configured to quickly absorb and pull liquid away from the body. Accordingly, the intake layer 32 can provide the function of liquid intake and can also provide the functions of liquid distribution, spreading, temporary storage and liquid retention. The intake layer may include natural fibers (e.g. woodpulp fluff), synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the absorbent body may include one or more components that can modify menses or intermenstrual liquid.

In a particular arrangement, the intake layer can be a thermally-bonded, stabilized-airlaid fibrous web (e.g. Concert code 175.1020) available from Concert Fabrication, a business having offices located in Gatineaux, Quebec, Canada. The intake layer may optionally be provided by a similar, stabilized airlaid fibrous web available from Buckeye Technologies, Inc., a business having offices located in Memphis, Tenn., U.S.A.

In a desired feature, the intake layer 32 can have a relatively lower basis weight, as compared to the bottom (garment-side) retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36. Alternatively, the basis weight of the intake layer can be higher than or equal to the basis weight of the shaping/retention layer 36.

In a particular aspect, the basis weight of the intake layer 32 can be at least a minimum of about 30 g/m$^2$. The basis weight of the intake layer can alternatively be at least about 100 g/m$^2$, and can optionally be at least about 120 g/m$^2$ to provide improved performance. In other aspects, the basis weight of the intake layer can be up to a maximum of about 250 g/m$^2$, or more. The basis weight of the intake layer can alternatively be up to about 200 g/m$^2$, and can optionally be up to about 175 g/m$^2$ to provide improved effectiveness.

In a desired feature, the top (bodyside) intake layer 32 of the present invention can be smaller in size than the bottom retention/shaping layer 36. Accordingly, the bottom retention/shaping layer 36 can be larger than the top intake layer, and can substantially define the overall size of the absorbent body 30. Optionally, the bottom retention/shaping layer 36 can be substantially equal to, or relatively smaller than the top intake layer.

The intake layer can be substantially centered (in its machine-direction and cross-direction) with respect to the shaping layer. Optionally, the intake layer may be skewed or offset in one direction (e.g. along the machine-direction), depending on where liquid is expected to first enter the absorbent article.

The top intake layer 32 may have any operative shape and/or design. For example, the intake layer may include a single piece of material, or multiple pieces of material. For example, the intake layer may include multiple strips of material. In addition, the intake layer 32 may include holes or apertures to better provide desired liquid-intake properties. The apertures may extend partially or completely through the z-directional thickness of the intake layer 32, as desired.

The shaping layer 36 can provide the functions of liquid storage and retention, liquid distribution, liquid spreading and shape maintenance. The shaping layer may include natural fibers (e.g. woodpulp fluff), synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer may include one or more components that can modify the menses or intermenstrual liquid.

In a particular arrangement, the shaping layer can be a thermally-bonded, stabilized-airlaid fibrous web available from Concert Fabrication (e.g. Concert code 225.1021), a business having offices located in Gatineaux, Quebec, Canada. The shaping layer 36 may optionally be provided by a similar, stabilized airlaid fibrous web available from Buckeye Technologies, Inc., a business having offices located in Memphis, Tenn., U.S.A.

In a particular aspect, the basis weight of the shaping layer 36 can be at least a minimum of about 100 g/m$^2$. The shaping layer basis weight can alternatively be at least about 130 g/m$^2$, and can optionally be at least about 165 g/m$^2$ to provide improved performance. In other aspects, the basis weight of the shaping layer can be up to a maximum of about 400 g/m$^2$, or more. The shaping layer basis weight can alternatively be up to about 350 g/m$^2$, and can optionally be up to about 325 g/m$^2$ to provide improved effectiveness. In a desired configuration, the shaping layer basis weight can be about 225 g/m$^2$.

Further details regarding a suitable absorbent and absorbent system are described in U.S. Patent Application Publication 2004/0186448, which was published Sep. 23, 2004. The entire disclosure of this document is incorporated herein by reference in a manner that is consistent herewith.

The personal care article 20 can further include a garment-attachment mechanism operatively connected to a garment-side of the backsheet layer 28. In a desired feature, a selected configuration of a garment-attachment mechanism may be distributed onto the garment-side of the article to help secure the article to the undergarment. Any operative fastening or attachment mechanism may be employed. The garment-attachment may, for example, include an interengaging mechanical fastener, a hook-and-loop fastener, a cohesive fastener, an adhesive fastener or the like, as well as combinations thereof. In particular aspects, the garment-attachment mechanism may include an adhesive 38, and the garment-attachment mechanism can be arranged in any operative configuration, such as the illustrated strip regions. Typically, the garment adhesive can be distributed over the garment-side of the backsheet, and one or more layers or sheets of release material 40 can be removably placed over the garment adhesive during storage, prior to use. In other aspects, the garment-attachment mechanism and/or release material can be arranged to reduce any excessive interference with the desired folding of the article about the selected fold lines and fold regions.

The article 20 can include a system of side-panel or wing portions 42 which can be integrally connected to appointed sections of the side regions along the intermediate portion of the article. For example, the side-panels or wings can be separately provided members that are subsequently attached or otherwise operatively joined to the intermediate portion of the article 20. In other configurations, the wings or side-panels 42 can be unitarily formed with one or more components of the article. As representatively shown in FIGS. 2, 2A and 2B, for example, either or both wing portions may be integrally formed from a corresponding, operative extension of the material employed to form the topsheet 26. Alternatively, either or both wing portions may be formed from a corresponding, operative extension of the material employed to form the backsheet 28, or formed from a corresponding, operative combination of the topsheet and backsheet materials.

The side-panels can have an appointed storage position (e.g. FIG. 4) in which the side-panels 42 are directed generally inwardly toward the longitudinally-extending centerline 52, in configurations that are well known in the art. The storage position can be configured with the side-panels extending generally adjacent to the garment-side of the backsheet layer 28. Alternatively, the storage position can be configured with the side-panels extending generally adjacent to the bodyside of the topsheet 26. The side-panel that is connected to one side margin of the article may optionally have sufficient cross-directional length to extend and continue past the centerline 52 to approach the laterally opposite side margin of the article. The storage position of the side-panels can ordinarily represent an arrangement observed when the article is first removed from its wrapper or other packaging. Prior to placing the article into a bodyside of an undergarment prior to use, the side-panels 42 can be selectively arranged to extend laterally outboard at the side regions of the article intermediate portion (e.g. FIGS. 2 and 2A). After placing the article in the crotch-region of the undergarment, the side-panels 42 can be operatively wrapped and secured around the side edges of the undergarment to help hold the article in place.

The side-panel portions 42 can have any operative construction, and can include a layer of any operative material. Additionally, each side-panel can comprise a composite material. For example, the side-panels may include a spunbond fabric material, a polymer film material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region of the article in any operative manner. For example, the side-panel can be joined to the topsheet 26, the backsheet 28 or another article component, as well as any combination thereof. In the illustrated example, each side-panel 42 is joined to the outward, garment-side surface of the backsheet 28, but may optionally be joined to the bodyside surface of the backsheet. The side-panel can be attached with hotmelt adhesive, but any other operative adhesive or attachment mechanism may alternatively be employed.

In another feature, each side-panel portion 42, or any desired combination of the employed side-panel portions, can include a panel-fastener mechanism 50 which is operatively joined to an appointed engagement surface of its associated side-panel. The panel-fastener can be configured to operatively attach to the wearer's undergarment and/or to any appointed, landing-zone portion of the article 20. For example, the panel-fastener can include a system of interengaging mechanical fasteners, a system of adhesive fasteners, a system of cohesive fasteners or the like, as well as combinations thereof.

Either or both side-panels 42 may include a panel-fastener component 44 which includes a hook or other "male" component of an interengaging mechanical fastener system. Any operative hook component may be employed. For example, a suitable hook component material can include a J-hook, mushroom-head hook, flat-top nail-head hook, a palm-tree hook, a multiple-J hook or the like, as well as combinations thereof. Alternatively, either or both side-panels 42 can include a panel-fastener component 44 which alternatively incorporates an operative adhesive. The adhesive may be a solvent-based adhesive, a hotmelt adhesive, a pressure-sensitive adhesive, or the like, as well as combinations thereof. Each section of the adhesive or other fastener-component 44 may be covered with a readily removable release sheet 51.

Further details regarding a suitable panel-fastener system are described in U.S. Patent Application Publication 2004/0186448, which was published Sep. 23, 2004. The entire disclosure of this document is incorporated herein by reference in a manner that is consistent herewith.

In optional arrangements, the article 20 may include additional components or component layers, as desired. For example, a transfer layer may be positioned between the intake layer 32 and the shaping layer 36. In another feature, the article may include any desired pattern of embossments formed into at least the bodyside surface of the article. The embossing can deform the bodyside of the topsheet and can deform selected portions of the absorbent body 30 to provide operative channel regions that can help block, direct or otherwise control a desired movement of liquids along the bodyside surface of the article. The embossing can also provide an aesthetic benefit to the consumer, and a visual cue regarding fit and leakage protection. In particular arrangements, the embossments can be positioned generally adjacent the perimeter edges of the absorbent body 30. In other aspects, the embossments can be configured to provide a regular or irregular pattern having one or more channels which are distributed in a symmetrical or asymmetrical array, as desired.

With reference to FIGS. 3 through 5B, at least a portion of the first end-section 72 can be folded along or can otherwise be configured to include a first, end-fold-region 64 which is substantially convex along a backsheet-side of the article. Additionally, the first end-fold-region 64 can be configured to be substantially concave along a topsheet-side of the article 20. For example, the first end-section 72 can be folded along a first, transverse fold-line 84 that extends along the lateral, cross-direction 24 of the article to provide the desired configurations of the first end-fold-region 64.

At least a portion of the second end-section 72a can be folded along or can otherwise be configured to include a second, end-fold-region 66 which is substantially convex along the backsheet-side of the article. Additionally, the second end-fold-region 66 can be substantially concave along the topsheet-side of the article 20. For example, to provide the desired configurations of the second end-fold-region 66, the second end-section 72a can be folded along a second, transverse fold-line 86 that extends along the lateral, cross-direction 24 of the article.

The first laterally-extending, transverse end-fold-region 64 can be configured to be substantially convex along the backsheet-side of the article along at least a major portion of a lateral width that corresponds to the first end-fold-region. In a particular aspect, the first end-fold-region can be configured to be substantially convex on the backsheet-side of the article along at least about 65% of the corresponding lateral width of the first end-fold-region. The first end-fold-region can alternatively be configured to be substantially convex on the backsheet-side of the article along at least about 70% of the lateral width of the first end-fold region 64, and can optionally be configured to be substantially convex on the backsheet-side of the article along at least about 80% of the lateral width of the first end-fold region 64 to provide desired benefits.

In addition, the second laterally-extending, transverse end-fold-region 66 can be configured to be substantially convex along the backsheet-side of the article along at least a major portion of a corresponding lateral width of the second end-fold-region. In a particular aspect, the second end-fold-region can be configured to be substantially convex on the backsheet-side of the article along at least about 65% of the corresponding lateral width of the second end-fold-region. The second end-fold-region 66 can alternatively be configured to be substantially convex on the backsheet-side of the article along at least about 70% of the lateral width of the second end-fold region, and can optionally be configured to be substantially convex on the backsheet-side of the article along at least about 80% of the lateral width of the second end-fold region 66 to provide desired benefits.

The first, laterally extending, end-fold-region can be positioned along a first, laterally-extending, fold-line 84, and the second, laterally extending, end-fold-region can be positioned along a second, laterally-extending, fold-line 86. The first, laterally extending, fold-line 84 can be spaced from a first terminal end-edge 90 of the article 20 by a first spacing distance 78. Similarly, the second, laterally extending fold-line 86 can be spaced from a longitudinally-opposed, second terminal end-edge 92 of the article 20 by a second spacing distance 80. Desirably, the first spacing distance can be approximately one-third of an overall longitudinal length 94 of the article 20, and the second spacing distance can be approximately one-third of the overall, longitudinal length 94 of the article 20. Thus, the first and second, laterally-extending fold-lines can be configured to trisect a longitudinal length of the article into three sections having approximately equal section-lengths along the longitudinal direction.

In other aspects, at least an operative portion of the first end-section 72 has been folded along a first, lengthwise-fold-region 58, which is positioned to extend longitudinally along a major portion of the first end-section. In desired arrangements, the first, lengthwise-fold-region 58 can be configured to extend discontinuously or substantially continuously along at least about 65% of the corresponding longitudinal length of the first end section 72 of the article. The first lengthwise-fold-region 58 can alternatively be configured to extend discontinuously or substantially continuously along at least about 70%, and optionally along at least about 80% or 90% of the longitudinal length of the first end section 72 to provide desired benefits. In a representatively shown feature, the first, longitudinally extending, lengthwise-fold-region 58, can be positioned to extend along substantially the entire distance between the first end-fold-region 64 and a first terminal end-edge 90 of the article 20.

Similarly, at least an operative portion of said second end-section 72a has been folded along a second, lengthwise-fold-region 62, which is positioned to extend longitudinally along a major portion of the second end-section. The second, lengthwise-fold-region 62 can be configured to extend discontinuously or substantially continuously along at least about 65% of the corresponding longitudinal length of the second end section 72a of the article. The second end-fold-region can alternatively be configured to extend discontinuously or substantially continuously along at least about 70%, and optionally along at least about 80% or 90% of the longitudinal length of the second end section 72 to provide further desired benefits. In a representatively shown feature of the article, the second, longitudinally-extending, lengthwise-fold-region 62 can be positioned to extend along substantially the entire distance between the second end-fold-region 66 and a second terminal end-edge 92 of the article 20.

In another aspect, at least an operative portion of the intermediate-section 76 has been folded along a third lengthwise-fold-region 68, which is positioned to extend longitudinally along a major portion of the intermediate-section. The third, lengthwise-fold-region 68 can be configured to extend discontinuously or substantially continuously along at least about 65% of the corresponding longitudinal length of the intermediate section 76 of the article. The second end-fold-region can alternatively be configured to extend discontinuously or substantially continuously along at least about 70%, and optionally along at least about 80% or 90% of the longitudinal length of the article intermediate-section 76 to provide further desired benefits. In a representatively shown feature, the third, longitudinally-extending, lengthwise, intermediate-fold-region 68 can be positioned to extend along substantially the entire distance between the first end-fold-region 64 and the second end-fold-region 66.

In further aspects, the first lengthwise-fold-region 58 has been folded in a first, fold-direction, the second lengthwise-fold-region 62 has been folded in a second, fold-direction, and the intermediate, third lengthwise-fold-region 68 has been folded in a third, fold-direction. The first fold-direction is substantially the same as the second fold-direction, and the third fold-direction is substantially opposite the first fold-direction. Additionally, the third fold-direction can also be substantially opposite the second fold-direction.

In desired aspects, each of the first, second and/or third lengthwise-fold-regions (58, 62, and/or 68) can be substantially aligned with and may substantially lie along the longitudinally-extending centerline 52 of the article. Additionally, each of the individual first, second and/or third lengthwise-fold-regions (58, 62, and/or 68) can longitudinally extend discontinuously or substantially continuously along the entirety of its corresponding, individual length. Each lengthwise-fold-region may or may not extend substantially contiguously with its immediately adjacent lengthwise-fold-region.

Typical personal care articles, such as menstrual and incontinent pad products, can deform uncontrollably in use. This uncontrolled deformation can lead to excessive leakage as the product shifts and bunches. A distinctive pre-folding of the article can significantly reduce the unwanted shifting and bunching of the article during ordinary use. Particular features of distinctive folding patterns can also help provide lateral shaping in predetermined regions along the length and width of the article.

In particular configurations, the first lengthwise-fold-region 58 can be substantially concave along a topsheet side of the article 20, and can be substantially convex along a backsheet side of the article (e.g. FIG. 7A). Additionally, the second lengthwise-fold-region 62 can be substantially concave along the topsheet-side of the article 20, and can be substantially convex along the backsheet-side of the article. In a further feature, the third lengthwise-fold-region 68 can be substantially concave along the backsheet-side of the article and substantially convex along the topsheet-side of the article (e.g. FIG. 7B).

The pattern of folds can provide a convex or close-to-body fit in the target area of the article, which ordinarily receives the initial discharge of bodily liquids. Thusly configured, the intermediate section of article can provide a generally tent-shaped arrangement with an apex, or top of the tent-shape positioned on the bodyside of the article, which is ordinarily appointed for a relatively closer placement against a wearer's body. This close-to-body shaping can be desirable when the article is employed to handle menstrual or other vaginal liquids. The close-to-body shaping can be enhanced when the wearer's legs compress the sides of the article. The compressing of the article sides can also help rotate the article end-sections rotate towards the wearer's body during use. In addition, the folding pattern can help form a more away-from-the-body fit in the back end-section of article. This type of fit in the rear end-section can help prevent it from undesirably entering the gluteal cleft.

Figure 9:
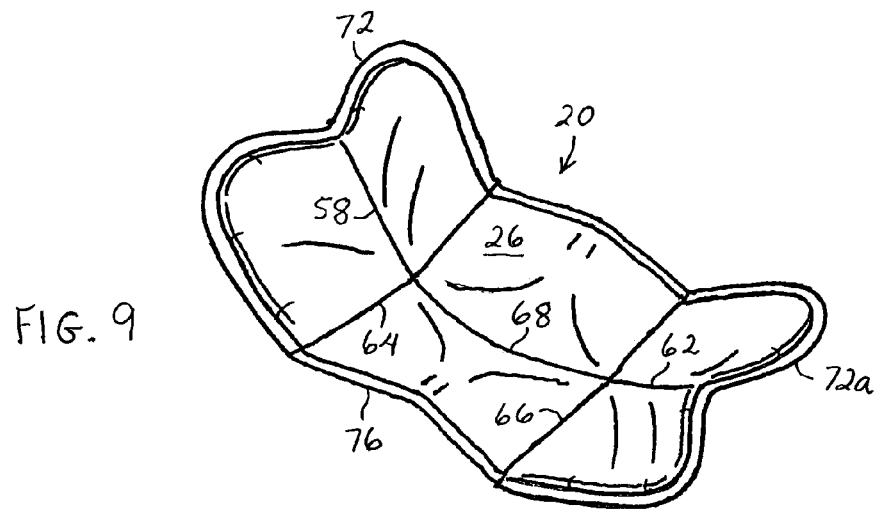
FIG. 9 shows a representative, perspective view of a partially unfolded article that has been subjected to the second arrangement of the composite folding operation.
Figure 9A:
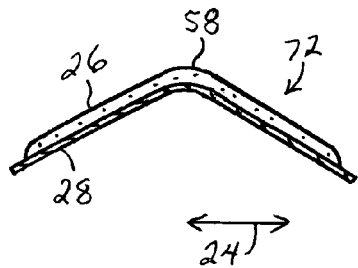
FIG. 9A shows a representative, cross-sectional view of an end section of an article that includes a corresponding, lengthwise fold-region produced by the second, composite folding operation.

The article 20 can alternatively have a configuration in which the first lengthwise-fold-region 58 is substantially convex along a topsheet side of the article 20 and substantially concave along a backsheet side of the article (e.g. FIG. 9A). Additionally, the second lengthwise-fold-region 62 can also be substantially convex along the topsheet-side of the article and substantially concave along the backsheet-side of the article. In a further feature, the third lengthwise-fold-region 68 can be configured to be substantially convex along the backsheet-side of the article 20 and substantially concave along the topsheet-side of the article (e.g. FIG. 9B).

The pattern of folds can form a "bucket" or "trough" in the target area of the article, which ordinarily receives the initial discharge of bodily liquids. Thusly configured, the intermediate section of the article can provide a bucket or trough-shaped arrangement with a bottom of the trough-shape appointed for a relatively further placement away from a wearer's body. As a result, the intermediate section of the article can provide a relatively larger void space that can rapidly accommodate large surges of discharged liquids. The trough-shape in the article intermediate section can be desirable when the article is employed to handle adult incontinence. When the wearer's legs compress the sides of the pad, the bucket or trough-shape can be enlarged, and the bottom of the trough-shape in the intermediate-section of the article can move further away from the wearer's body.

In the various arrangements of the article 20, the first lengthwise-fold-region 58 can be positioned between, and significantly spaced from each of the terminal side-edges 61 of the article in the first end-section 72 of the article. In addition, the second lengthwise-fold-region 62 can be positioned between, and significantly spaced from the terminal side-edges of the article in the second end-section 72a of the article. Similarly, the third lengthwise-fold-region 62 can be positioned between, and significantly spaced from both of the terminal side-edges 61 of the article in the intermediate-section 76 of the article. As representatively shown, the third lengthwise-fold-region 68 can be positioned in a medial section of the article, and is located between the terminal side-edges of the article in the intermediate-section 76 of the article.

In a particular feature, the first lengthwise-fold-region 58 can be substantially aligned with the third lengthwise-fold-region 68; and the second lengthwise-fold-region 62 can also be substantially aligned with the third lengthwise-fold-region 68. In another feature, the first lengthwise-fold-region 58 can be substantially contiguous with the third lengthwise-fold-region 68; and the second lengthwise-fold-region 62 can be substantially contiguous with the third lengthwise-fold-region 68.

In a desired arrangement, the first end-fold-region 64 of the article has been configured to be convex along the backsheet-side of the article along approximately 100% of the corresponding lateral width of the first end-fold-region, and the second end-fold-region 66 has been configured to be convex along the backsheet-side of the article along approximately 100% of the corresponding lateral width of the second end-fold-region. The first, laterally extending, end-fold-region 64 can also be positioned along a portion of the first end-section 72 which is immediately adjacent, or at least proximally adjacent the intermediate-section 76 of the article, and the first end-fold region 64 can be operatively arranged to provide a folded-over first end-section which is positioned relatively closely adjacent to, or directly onto the intermediate-section 76. The second, laterally extending, end-fold-region 66 can be positioned along a portion of the second end-section 72a which is immediately adjacent or at least proximally adjacent the intermediate-section 76 of the article, and the second end-fold region 66 can be operatively arranged to provide a folded-over second end-section which is positioned relatively closely adjacent to, or directly onto the folded-over first end-section, thereby providing a preliminary-folded article 82. In addition, the preliminary-folded article 82 can be further folded along a longitudinally-extending, composite fold-line 74 to thereby provide a composite-folded article 88.

Figure 5:
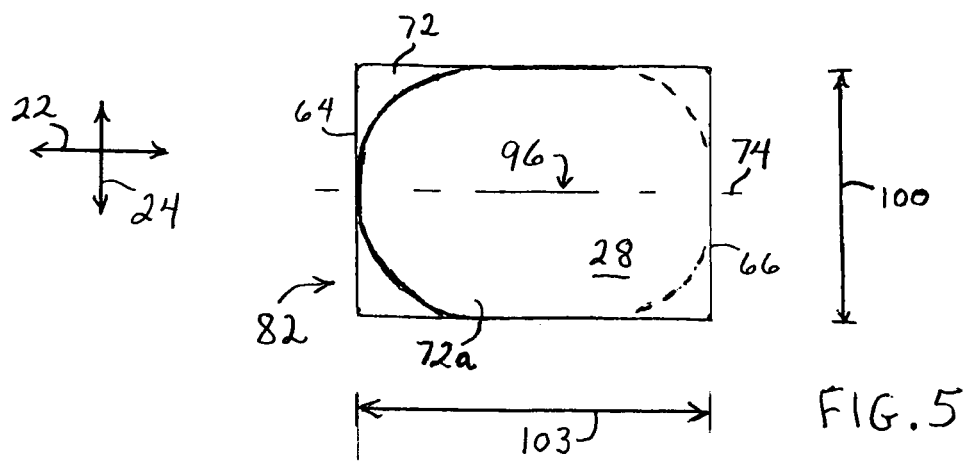
FIG. 5 shows a representative, plan view of a preliminary-folded article that has been folded about a first, laterally-extending fold-region and further folded about a second, laterally-extending fold-region.
Figure 5A:
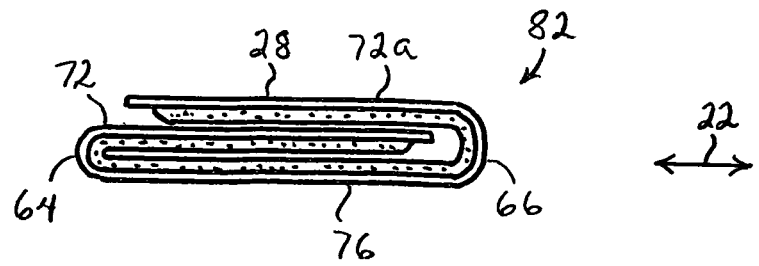
FIG. 5A shows a representative, elevational side view of the preliminary-folded article of FIG. 5.
Figure 5B:
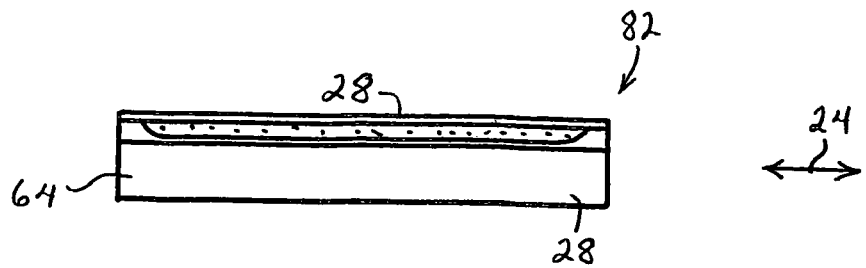
FIG. 5B shows a representative, end view of the preliminary-folded article illustrated in FIG. 5.
Figure 8:
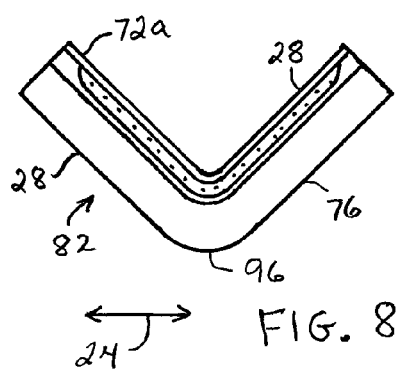
FIG. 8 shows a representative, schematic, end view of an article that has been partially subjected to a second, alternative arrangement of the composite folding operation to provide another, alternative composite-fold-region.
Figure 8A:
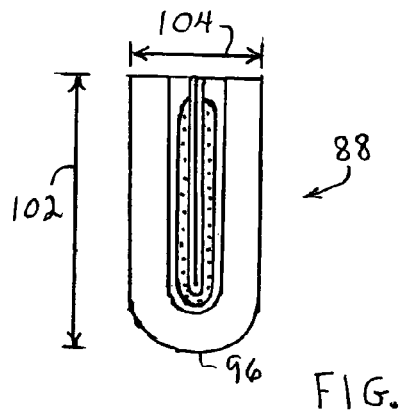
FIG. 8A shows a representative, schematic, end view of an article that has been completely subjected to the second, composite folding operation.

As representatively shown in FIGS. 5 through 5B, the folded-over, first end-section 72 can be sandwiched between the article intermediate section 76 and the folded-over, second end-section 72a. Additionally, a first, topsheet portion in the folded-over first end-section 72 can be positioned indirectly or directly onto an intermediate topsheet portion in the intermediate-section 76 of the article 20. Additionally, a second-topsheet portion in the folded-over second end-section 72a can be positioned indirectly or directly onto a first, backsheet portion in the folded-over first end section 72.

As representatively illustrated in FIGS. 5 through 6A, the preliminary-folded article 82 can be folded along said longitudinally-extending, composite fold-line 74 to provide a composite-fold-region 96 which is substantially convex along the backsheet-side of the intermediate section 76 of the article. In this arrangement of the composite-fold-region, each of the article end-sections 72, 72a can be substantially concave along the backsheet-sides of the article end-sections.

Alternatively, as representatively shown in FIGS. 5-5B, 8 and 8A, the preliminary-folded article 82 can be folded along the longitudinally extending, composite fold-line 74 to provide a composite fold region 96 which is substantially concave along the backsheet-side of the intermediate section 76 of the article. In desired arrangements, the longitudinally extending, composite fold-line 74 can be operatively arranged to approximately bisect the preliminary-folded article 82 relative to the article width along the lateral cross-direction of the article.

The preliminary-folded article 82 can be subjected to any operative arrangement of a composite folding operation to provide a suitable composite-fold-region 96. With reference to FIGS. 5, 5B, 6 and 6A, for example, a first arrangement of the composite folding operation can bend the preliminary-folded article 82 about the longitudinally extending, composite fold-line 74 in a first direction. When subjected to the first composite folding operation, the lengthwise folded intermediate-section 76 can be substantially sandwiched between the lengthwise folded end-sections 72, 72a. At least one of the lengthwise folded end-sections will be positioned on an outermost side of the composite-folded article 88. The first composite folding operation can configure the outermost, article end-section (e.g. end-section 72a) such that the backsheet-side of the outermost end-section is convex in the corresponding composite-folded article 88. Additionally, the first composite folding operation can configure the article intermediate section 76 such that the backsheet-side of the article intermediate-section is concave in the composite-folded article.

With reference to FIGS. 7 through 7B, the composite-folded article 88 can be subsequently rearranged to an at least partially unfolded condition for ordinary use. The at least partially unfolded condition can have a corresponding three-dimensional configuration that is produced or otherwise derived from the first composite folding operation. In a particular feature, each article end-section (72, 72a) can be at least partially bent about its corresponding lengthwise fold-region (58, 62) in a configuration where the backsheet-side of the bent end-section is convex and the topsheet-side of the bent end-section is concave. In another feature, the article intermediate-section 76 can be at least partially bent about its corresponding lengthwise fold-region 68 in a configuration where the backsheet-side of the bent intermediate-section is concave and the topsheet-side of the bent intermediate-section is convex.

As representatively shown in FIGS. 5, 5B, 8 and 8B, a second, alternative arrangement of the composite folding operation can bend the preliminary-folded article 82 about the longitudinally extending, composite fold-line 74 in a second direction. When subjected to the second composite folding operation, the lengthwise folded end-sections 72, 72a can be substantially sandwiched between the lengthwise folded intermediate-section 76. At least one of the lengthwise folded end-sections will be positioned on an innermost side of the composite-folded article 88. The second composite folding operation can configure the innermost, article end-section (e.g. end-section 72a) such that the backsheet-side of the innermost end-section is concave when arranged in the corresponding composite-folded article 88. Similarly, the second composite folding operation can configure the other article end-section (e.g. end-section 72) such that the backsheet-side of the other end-section is concave in the corresponding composite-folded article 88. In addition, the second composite folding operation can configure the article intermediate section 76 such that the backsheet-side of the article intermediate-section is convex in the composite-folded article.

Figure 9B:
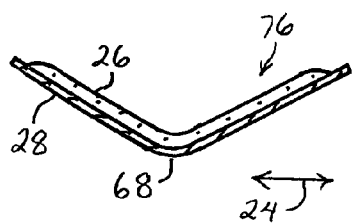
FIG. 9B shows a representative, cross-sectional view of an intermediate section of an article that includes a corresponding, lengthwise, intermediate fold-region produced by the second, composite folding operation.

With reference to FIGS. 9 through 9B, the composite-folded article 88 can be subsequently rearranged and at least partially unfolded for ordinary use. The at least partially unfolded condition can have a corresponding three-dimensional configuration that is produced or otherwise derived from the first composite folding operation. In a particular feature, each article end-section (72, 72a) can be at least partially bent about its corresponding lengthwise fold-region (58, 62) in a configuration where the backsheet-side of the bent end-section is concave, and the topsheet-side of the bent end-section is convex. In another feature, the article intermediate-section 76 can be at least partially bent about its corresponding lengthwise fold-region 68 in a configuration where the backsheet-side of the bent intermediate-section is convex and the topsheet-side of the bent intermediate-section is concave.

With reference again to FIGS. 4-5B, the article may include a pair of laterally extending and laterally opposed wing portions 42, 42a, and the wing portions can be arranged in a storage position which is immediately adjacent or at least proximally adjacent a topsheet-side or backsheet side of the article. Additionally, the preliminary-folded article 82 can be folded along the longitudinally extending, composite fold-line 74 to provide a composite fold region 96 which is substantially concave along the backsheet-side of the intermediate section 76 of the article (e.g. FIGS. 6-6A). The preliminary-folded article 82 can alternatively be folded along the third, longitudinally extending, composite fold-line 74 to provide a composite fold region 96 which is substantially convex along the backsheet-side of the intermediate section 76 of the article (e.g. FIGS. 8-8A).

Where the article 20 includes at least a pair of laterally extending and laterally opposed side-panel or wing portions 42, 42a, the wing portions 42 can be arranged in a storage position, with the wing portions located adjacent a selected, outer surface of the article 20, and extending inboard towards the longitudinal centerline 52. As representatively shown, for example, the wing portions 42 can be configured to be substantially, immediately adjacent the topsheet-side of the article. Optionally, the wing portions 42 can be configured to be substantially, immediately adjacent the backsheet-side of the article.

Desirably, the folding of the article end sections (72, 72a) along the respective laterally-extending fold-lines (84, 86) can be conducted after placing the wings portions 42, 42a in their storage positions. The folding of the article end sections may optionally be conducted prior to placing the wings portions in their storage positions. The absorbent article 20 may have a configuration in which one or more of the laterally-extending fold-lines and fold-regions are positioned to extend through each individual wing portion. In a particular aspect, the absorbent article 20 may have a configuration in which at least one longitudinally-extending fold-line or fold-region is positioned to extend through each individual wing portion. In other aspects, the article can have a configuration in which none of the laterally-extending or longitudinally-extending fold lines (or fold regions) intersect the areas of the individual wing portions.

The various configurations of the personal care article 20 may be enhanced by making the appointed fold-regions (e.g.

fold-regions 58, 62, 64, 66, and/or 68) more flexible, extensible, stretchable or otherwise more foldable. For example, the topsheet 26, backsheet 28, absorbent body 30, garment-attachment mechanism 38, and/or release material 40 can be constructed with materials that are flexible, elastomerically extensible, plastically extensible or otherwise operatively stretchable. Further details regarding suitable constructions that can enhance the desired folding ability are described in U.S. Pat. Nos. 5,611,790; 5,197,959; and 4,950,264; and in U.S. Patent Application 2005/0182374. The entire disclosures of these documents are incorporated herein by reference in a manner that is consistent herewith.

The article 20 can also be configured to have a selected, overall article length 94, an overall article width 100, and an overall article thickness 25, as determined when the article is in its flat-out condition with substantially all gathering and/or folding removed, (e.g. FIGS. 3-5) to help provide desired benefits. In a particular aspect, the article length can be not more than a maximum of about 325 mm. The article length can alternatively be not more than about 300 mm, and can optionally be not more than about 240 mm. In another aspect, the article width 100 can be not more than a maximum of about 100 mm. The article width can alternatively be not more than about 70 mm, and can optionally be not more than about 40 mm to provide desired benefits. In further aspect, the article thickness can be not more than a maximum of about 7 mm, as determined under a restraining pressure of 0.1 psi (0.7 KPa). The article thickness can alternatively be not more than about 5 mm, and can optionally be not more than about 2.5 mm. When the article length and thickness are within the desired values, the article can provide improved discretion and comfort.

The composite-folded article 88 can have a selected length 103 (e.g. FIG. 5), a selected width 102 and a selected thickness 104 (e.g. FIG. 6A). The composite-folded thickness is determined under a restraining pressure of 0.1 psi (0.7 KPa). In a particular aspect, the composite-folded length 103 can be less than 10 cm to provide desired levels of discretion. The composite-folded length can alternatively be less than 7 cm, and can optionally be less than 4 cm to provide desired benefits. In another aspect, the composite-folded width 102 and thickness 104 have been configured to provide a selected girth, which extends around the composite-folded article and along the width and thickness dimensions of the composite-folded article. In desired arrangements, the composite-folded girth can be less than about 15 cm. The girth can alternatively be less than 10 cm, and can optionally be less than about 5 cm to provide improved benefits. In a particular arrangement, the composite-folded girth can be less than about 15 cm and the composite-folded length can be less than about 10 cm. Another arrangement of the composite-folded article can have a girth that is less than about 10 cm and a length that is less than about 7 cm. In a further arrangement, the girth can be less than about 5 cm and the length can be less than about 4 cm.

The selected length and girth dimensions of the composite-folded article 88 can help provide improved discretion and convenience. By incorporating the length and girth dimensions, the composite-folded article can be more discreetly hidden in a user's hand, and can be more discreetly carried and transported.

Figure 10:
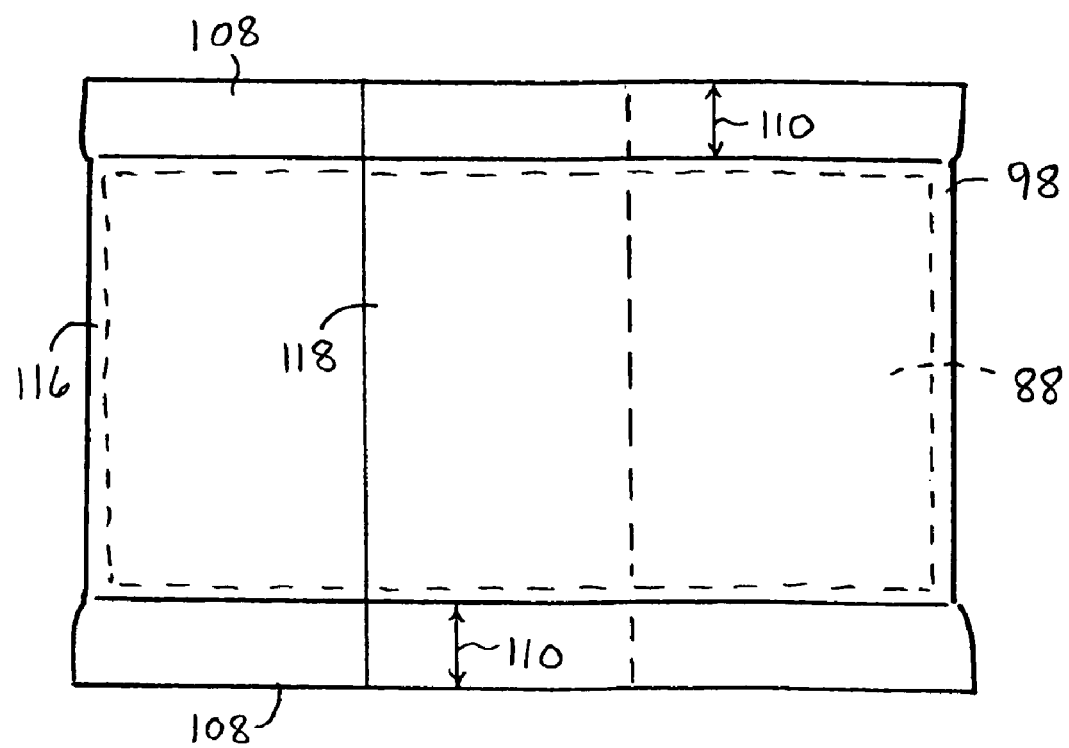
FIG. 10 shows a partially cut-away, plan view of a representative preliminary-folded article contained in a pouch or other wrap member.
Figure 10A:
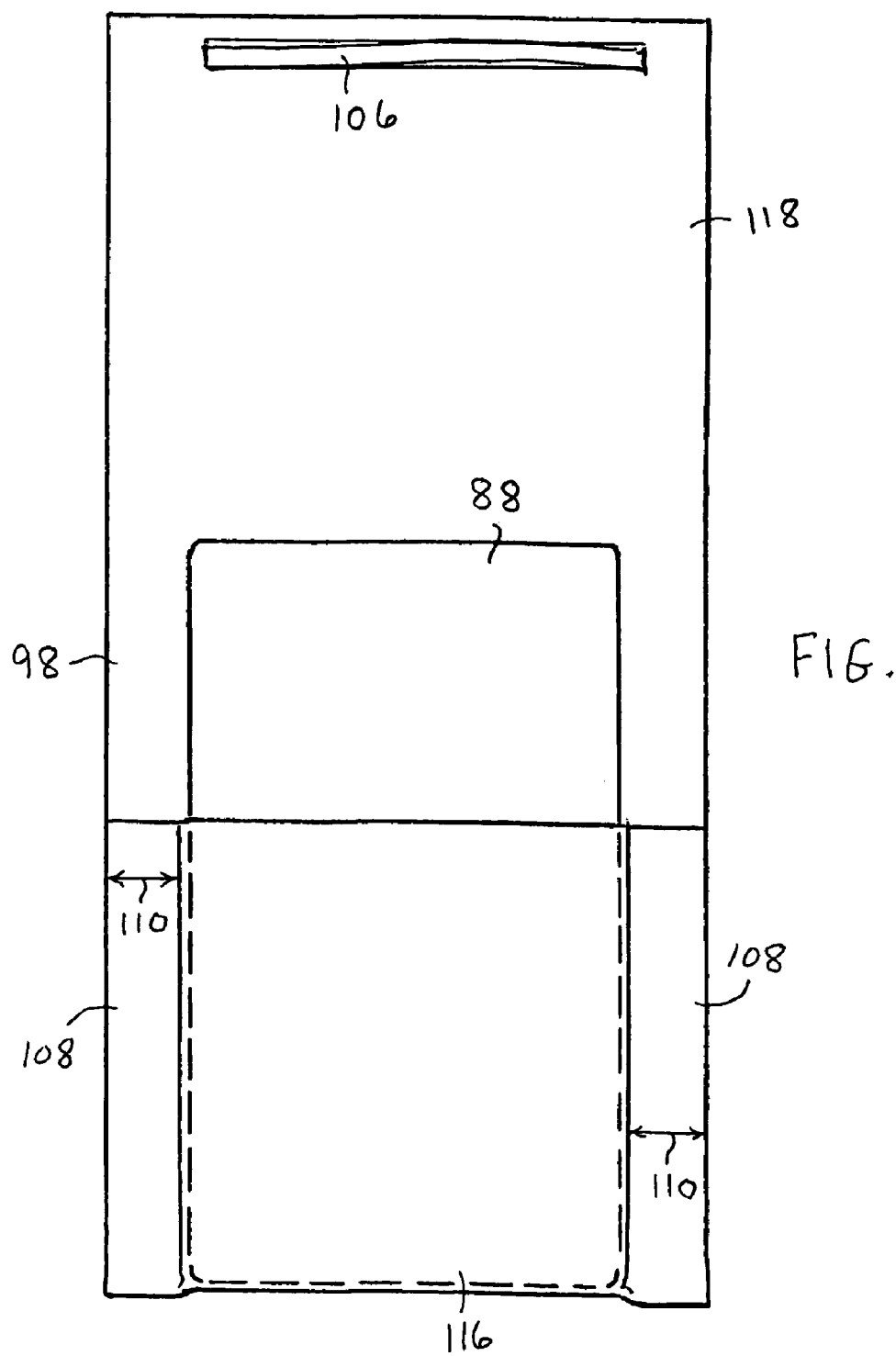
FIG. 10A shows a partially cut-away, plan view of a representative composite-folded, wrapped article that can be provided from the arrangement illustrated in FIG. 10.
Figure 11:
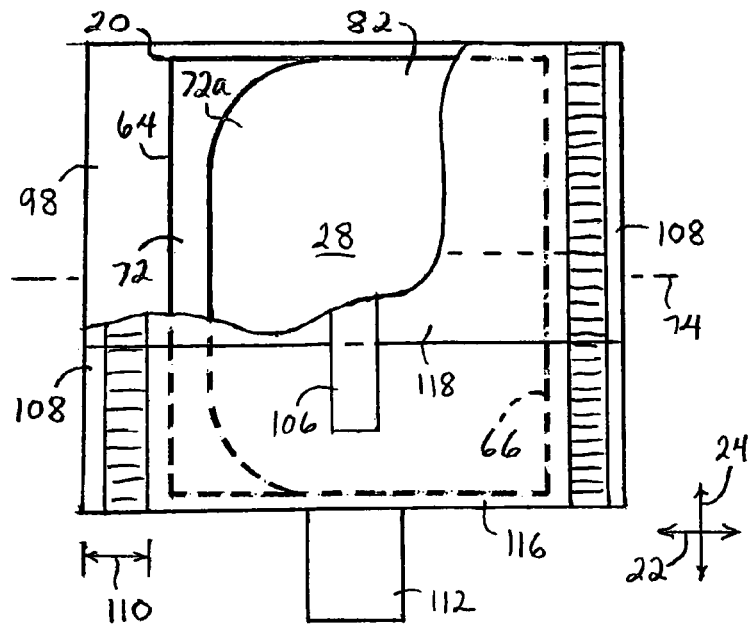
FIG. 11 shows a representative arrangement of an article contained in a pouch or other wrap member.
Figure 11A:
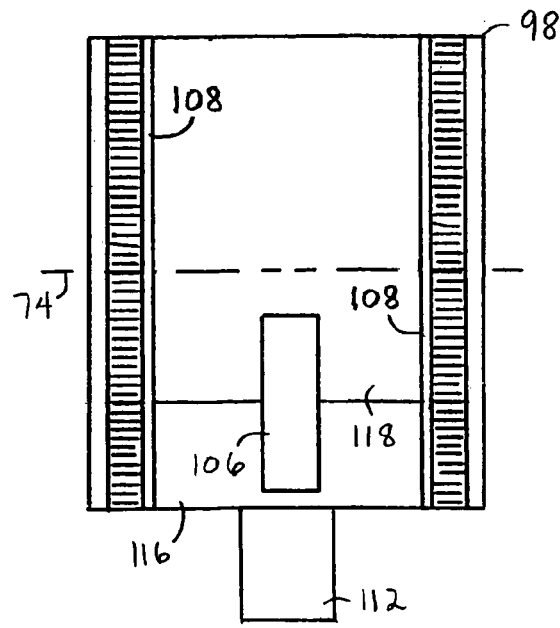
FIG. 11A representatively shows a wrapped article in which side margins of the wrap member have been inwardly folded onto a container portion of the wrap member.

With reference to FIGS. 10-11, the personal care article 20 can further include a pouch member or other wrap member 98 which can operatively enclose at least a major portion or an otherwise significant portion of the personal care article 20 in its folded condition (e.g. the preliminary-folded article 82 and/or the composite-folded article 88). The wrap member 98 can be configured to provide a container-portion 116, a flap section 118, and at least one, outboard-extending, wrap side-margin 108. Additionally, the wrap member can include a flap closure mechanism 106, which can operatively hold the flap section 118 in a substantially closed position. The flap closure mechanism can be provided by any operative device or system. For example, the flap closure mechanism can include an interengaging mechanical fastener, a hook-and-loop fastener, a cohesive fastener, an adhesive fastener or the like, as well as combinations thereof. As illustrated, the flap closure mechanism 106 may be indirectly connected to the wrap member, such as by employing a separately provided tab member. Alternatively, the flap closure mechanism may be formed with or otherwise directly connected to the wrap member.

As representatively shown, the pouch member or other wrap member can have a system of one or more side-margins, such as the illustrated pair of opposed side-margins 108. Each side margin can include a closure seam, and each closure seam can be arranged with any operative distribution or pattern. In a particular feature, the closure seam can have a distinctively small width dimension 110. In a particular aspect, the width of the closure seam can be not more than a maximum of about 2 cm. The side-margin or seam width 110 can alternatively be not more than about 1 cm, and can optionally be not more than about 0.5 cm. The selected width of a side-margin seam of the pouch or other wrap member can help provide improved discretion and convenience. By incorporating the selected side-margins and seam widths, the operative container that holds the composite-folded article 88 can be more discreetly hidden in a user's hand, and can be more discreetly carried and transported.

In particular aspects, one or more of the side-margins 108 can extend generally along the longitudinal-direction 22, with an alignment that is generally parallel to the appointed, composite fold line 74 of the personal care article and pouch member or other wrap member. Accordingly, the first and second lengthwise fold-regions 58, 62 can be configured to be generally parallel to the longitudinally extending side-margins of the pouch or wrap member. Alternatively, one or more of the side-margins 108 can extend generally along the transverse, cross-direction 24, with an alignment that is generally perpendicular to the appointed, composite fold line 74 of the personal care article and pouch member or other wrap member.

With reference to FIGS. 11-12B, at least one of the side-margins 108 and any associated closure seams of the wrap member 98 can be folded to face against the container-portion of the wrap member, and can be operatively attached to the wrap container-portion 116. The at least one of the side-margins or closure seams 108 of the wrap member 98 may have been folded to face against the container-portion 116 of the wrap member, before or after the folding of the preliminary-folded article 82 and wrap member 98 along their combined, composite fold-region 96a. Additionally, at least one of the side-margins or closure seams 108 of the wrap member 98 may have been operatively attached to the wrap container-portion 116, before or after the folding of the preliminary-folded article 82 and associated wrap member 98 along their combined, composite fold-region 96a. The flap section 118 of the wrap member may also have been placed in a closed-position prior to the folding of the preliminary-folded article 82 and wrap member 98 along the overall, composite fold-region 96a of the combined wrap member and preliminary-folded article.

The wrap retainer mechanism 112 can be provided by any operative device or system. For example, the wrap retainer mechanism can include an interengaging mechanical fastener, a hook-and-loop fastener, a cohesive fastener, an adhesive fastener or the like, as well as combinations thereof. As illustrated, the wrap retainer 112 may be indirectly connected to the wrap member, such as by employing a separately provided tab member. Alternatively, wrap retainer may be formed with or otherwise directly connected to the wrap member.

The composite-folded, wrapped article 114 can have a combined, overall composite-folded, wrapped length that is generally aligned with and generally corresponds to the length 103 of the preliminary-folded article 82; and a combined, overall composite-folded, wrapped width that is generally aligned with and generally corresponds to the width 102 of the composite-folded article 88. The composite-folded, wrapped article 114 can also have a combined, overall composite-folded, wrapped thickness that is generally aligned with and generally corresponds to the article thickness 104. The composite-folded, wrapped thickness also is determined under a restraining pressure of 0.1 psi (0.7 KPa). In a particular aspect, the composite-folded, wrapped length can be less than 10 cm to provide desired levels of discretion. The composite-folded, wrapped length can alternatively be less than 7 cm, and can optionally be less than 4 cm to provide desired benefits. In another aspect, the composite-folded, wrapped width and thickness have been configured to provide an overall composite-folded, wrapped girth, which extends around the complete composite-folded, wrapped article 114 and along the overall width and thickness dimensions of the composite-folded, wrapped article. In desired arrangements, the composite-folded, wrapped girth can be less than about 15 cm. The composite-folded, wrapped girth can alternatively be less than 10 cm, and can optionally be less than about 5 cm to provide improved benefits. In a particular arrangement, the composite-folded, wrapped girth can be less than about 15 cm and the composite-folded length can be less than about 10 cm. Another arrangement of the composite-folded, wrapped article can have an overall girth that is less than about 10 cm and an overall length that is less than about 7 cm. In a further arrangement, the overall girth can be less than about 5 cm and the overall length can be less than about 4 cm.

The selected length and girth dimensions of the composite-folded, wrapped article 114 can help provide improved discretion and convenience. By incorporating the length and girth dimensions, the composite-folded, wrapped article can be more discreetly hidden in a user's hand, and can be more discreetly carried and transported.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A personal care article having a longitudinal-direction; a relatively shorter lateral cross-direction; a first end-section; a second end-section; and an intermediate-section which is interposed between said first end-section and said second end-section; said article comprising:
   a liquid permeable topsheet layer; and
   a backsheet layer which is operatively connected to the topsheet layer;
   wherein
   at least an operative portion of said first end-section has been folded along a first laterally-extending, end-fold-region which is substantially convex along a backsheet-side of the article and extends along at least a major portion of a corresponding lateral width of the first end-fold-region;
   at least an operative portion of said second end-section has been folded along a second laterally-extending, end-fold-region which is substantially convex along the backsheet-side of the article and extends along at least a major portion of a corresponding lateral width of the second end-fold-region;
   at least an operative portion of said first end-section has been folded along a first, lengthwise-fold-region, which is positioned to extend longitudinally along a major portion of the first end-section;
   at least an operative portion of said second end-section has been folded along a second, lengthwise-fold-region, which is positioned to extend longitudinally along a major portion of the second end-section; and
   at least an operative portion of said intermediate-section has been folded along a third lengthwise-fold-region, which is positioned to extend longitudinally along a major portion of the intermediate-section, and wherein the third lengthwise-fold-region is substantially convex along the backsheet-side of the article and substantially concave along the topsheet-side of the article.

2. A personal care article as recited in claim 1, wherein
   the first lengthwise-fold-region has been folded in a first, fold-direction, the second lengthwise-fold-region has been folded in a second, fold-direction, and the third lengthwise-fold-region has been folded in a third, fold-direction;
   the first fold-direction is substantially the same as the second fold-direction; and
   the third fold-direction is substantially opposite the first fold-direction.

3. A personal care article as recited in claim 1, wherein
   the first end-fold-region has been configured to be substantially convex along the backsheet-side of the article along at least about 65% of a corresponding lateral width of the first end-fold-region; and
   the second end-fold-region has been configured to be substantially convex along the backsheet-side of the article along at least about 65% of a corresponding lateral width of the second end-fold-region.

4. A personal care article as recited in claim 1, wherein
   the first lengthwise-fold-region has been configured to extend along at least about 65% of a corresponding longitudinal length of the first end section; and
   the second lengthwise-fold-region has been configured to extend along at least about 65% of a corresponding longitudinal length of the second end section.

5. A personal care article as recited in claim 4, wherein
   the first lengthwise-fold-region is substantially aligned with the third lengthwise-fold-region; and
   the second lengthwise-fold-region is substantially aligned with the third lengthwise-fold-region.

6. A personal care article having a longitudinal-direction; a relatively shorter lateral cross-direction; a first end-section; a second end-section; and an intermediate-section which is interposed between said first end-section and said second end-section; said article comprising:
   a liquid permeable topsheet layer; and
   a backsheet layer which is operatively connected to the topsheet layer;
   wherein
   at least an operative portion of said first end-section has been folded along a first laterally-extending, end-fold-region which is substantially convex along a backsheet-side of the article and extends along at least a major portion of a corresponding lateral width of the first end-fold-region;

at least an operative portion of said second end-section has been folded along a second laterally-extending, end-fold-region which is substantially convex along the backsheet-side of the article and extends along at least a major portion of a corresponding lateral width of the second end-fold-region;

at least an operative portion of said first end-section has been folded along a first, lengthwise-fold-region, which is positioned to extend longitudinally along a major portion of the first end-section;

at least an operative portion of said second end-section has been folded along a second, lengthwise-fold-region, which is positioned to extend longitudinally along a major portion of the second end-section; and at least an operative portion of said intermediate-section has been folded along a third lengthwise-fold-region, which is positioned to extend longitudinally along a major portion of the intermediate-section, wherein the first end-fold-region has been configured to be convex along the backsheet-side of the article along approximately 100% of a corresponding lateral width of the first end-fold-region;

the second end-fold-region has been configured to be convex along the backsheet-side of the article along approximately 100% of a corresponding lateral width of the second end-fold-region;

the first, laterally extending, end-fold-region is positioned along a portion of the first end-section which is proximally adjacent the intermediate-section of the article, with the first end-fold region operatively arranged to provide a folded-over first end-section which is positioned onto the intermediate-section;

the second, laterally extending, end-fold-region is positioned along a portion of the second end-section which is proximally adjacent the intermediate-section of the article, with the second end-fold region operatively arranged to provide a folded-over second end-section which is positioned onto the folded-over first end-section, thereby providing a preliminary-folded article; and the preliminary-folded article has been folded along a longitudinally-extending, composite fold-line, thereby providing a composite-folded article, wherein the preliminary-folded article has been folded along said longitudinally-extending, composite fold-line to provide a composite fold region which is substantially convex along the backsheet-side of the intermediate section of the article.

7. A personal care article as recited in claim 6, wherein the longitudinally extending, composite fold-line operatively arranged to approximately bisect the preliminary-folded article relative to its width along the lateral cross-direction of the article.

8. A personal care article as recited in claim 6, wherein the article further includes a pair of laterally extending and laterally opposed wing portions;

the wing portions have been arranged in a storage position which is adjacent a topsheet-side or backsheet side of the article; and the preliminary-folded article has been folded along said longitudinally extending, composite fold-line to provide a composite fold region which is substantially convex along the backsheet-side of the intermediate section of the article.

9. A personal care article as recited in claim 1, wherein the composite-folded article has included a composite-folded girth which is less than about 15 cm and a composite-folded length which is less than about 10 cm.

10. A personal care article as recited in claim 1, further including a pouch member which operatively encloses at least a significant portion of the personal care article.

11. A personal care article as recited in claim 10, wherein the pouch member includes side margins with closure seams.

12. A personal care article as recited in claim 10, wherein the pouch member includes side margins which are generally parallel to a composite fold line of the personal care article and pouch member.

13. A personal care article as recited in claim 10, further including a wrap retainer mechanism.

14. A personal care article as recited in claim 1, further including an absorbent body which is operatively held between the topsheet layer and backsheet layer.

15. A personal care article having a longitudinal-direction; a relatively shorter lateral cross-direction; a first end-section; a second end-section; and an intermediate-section which is interposed between said first end-section and said second end-section; said article comprising:

a liquid permeable topsheet layer; and a backsheet layer which is operatively connected to the topsheet layer;

wherein at least an operative portion of said first end-section has been folded along a first laterally-extending, end-fold-region which is substantially convex along a backsheet-side of the article and extends along at least a major portion of a corresponding lateral width of the first end-fold-region;

at least an operative portion of said second end-section has been folded along a second laterally-extending, end-fold-region which is substantially convex along the backsheet-side of the article and extends along at least a major portion of a corresponding lateral width of the second end-fold-region;

at least an operative portion of said first end-section has been folded along a first, lengthwise-fold-region, which is positioned to extend longitudinally along a major portion of the first end-section;

at least an operative portion of said second end-section has been folded along a second, lengthwise-fold-region, which is positioned to extend longitudinally along a major portion of the second end-section; and at least an operative portion of said intermediate-section has been folded along a third lengthwise-fold-region, which is positioned to extend longitudinally along a major portion of the intermediate-section, wherein the first, laterally extending, end-fold-region is positioned along a first, laterally-extending, fold-line; the second, laterally extending, end-fold-region is positioned along a second, laterally-extending, fold-line; and the first and second, laterally-extending fold-lines have been configured to trisect a longitudinal length of the article into three sections having approximately equal section-lengths along the longitudinal direction.

* * * * *